US007214364B2

(12) United States Patent
Montgomery

(10) Patent No.: US 7,214,364 B2
(45) Date of Patent: *May 8, 2007

(54) INHALABLE AZTREONAM LYSINATE FORMULATION FOR TREATMENT AND PREVENTION OF PULMONARY BACTERIAL INFECTIONS

(75) Inventor: Alan Bruce Montgomery, Medina, WA (US)

(73) Assignee: Corus Pharma, Inc., Seattle, WA (US)

( * ) Notice: Subject to any disclaimer, the term of this patent is extended or adjusted under 35 U.S.C. 154(b) by 213 days.

This patent is subject to a terminal disclaimer.

(21) Appl. No.: 10/613,639

(22) Filed: Jul. 3, 2003

(65) Prior Publication Data

US 2004/0062721 A1  Apr. 1, 2004

Related U.S. Application Data

(63) Continuation-in-part of application No. 10/027,113, filed on Dec. 20, 2001, now Pat. No. 6,660,249.

(60) Provisional application No. 60/258,423, filed on Dec. 27, 2000.

(51) Int. Cl.
| | |
|---|---|
| *A61K 9/14* | (2006.01) |
| *A61K 31/15* | (2006.01) |
| *A61K 31/16* | (2006.01) |
| *A01K 31/16* | (2006.01) |
| *C07D 205/08* | (2006.01) |
| *C07D 205/09* | (2006.01) |
| *A01N 41/06* | (2006.01) |

(52) U.S. Cl. ............ 424/46; 514/210.03; 514/210.15; 514/837; 514/924; 514/932; 514/933; 514/951; 540/200; 540/355; 424/489

(58) Field of Classification Search .......... 514/210.03, 514/210.15, 924, 932, 933, 951, 837; 424/46, 424/489; 540/200, 355
See application file for complete search history.

(56) References Cited

U.S. PATENT DOCUMENTS

| | | | | |
|---|---|---|---|---|
| 4,550,105 | A | 10/1985 | Matsuo et al. | 514/210 |
| 4,572,801 | A | 2/1986 | Matsuo et al. | 260/245.4 |
| 4,610,824 | A | 9/1986 | Trū ner | 540/355 |
| 4,673,739 | A | 6/1987 | Matsuo et al. | 540/355 |
| 4,775,670 | A | 10/1988 | Sykes et al. | 514/210 |
| 4,822,788 | A | 4/1989 | Kishimoto et al. | 514/210 |
| 4,826,973 | A | 5/1989 | Anderson et al. | 540/335 |
| 4,888,998 | A | 12/1989 | Buzza et al. | 73/864.21 |
| 4,946,838 | A | 8/1990 | Floyd et al. | 514/210 |
| 5,875,776 | A | 3/1999 | Vaghefi | 128/203.15 |
| 5,994,340 | A | 11/1999 | Maiti et al. | 514/192 |
| 6,054,431 | A | 4/2000 | Horwitz et al. | 514/12 |
| 6,303,103 | B1 * | 10/2001 | Akehurst et al. | 424/45 |
| 6,518,239 | B1 | 2/2003 | Kuo et al. | 514/2 |

| | | | |
|---|---|---|---|
| 2004/0009126 | A1 | 1/2004 | Pilkiewicz .......... 424/46 |

FOREIGN PATENT DOCUMENTS

| | | | |
|---|---|---|---|
| EP | 0297580 | 1/1989 | 417/12 |
| EP | 0297580 A1 | 1/1989 | 417/12 |
| EP | 0297580 B1 | 1/1989 | 417/12 |
| EP | 0297580 | 1/1990 | 417/12 |
| EP | 0297580 | 1/1999 | 417/12 |
| WO | WO 0134232 | 5/2001 | |

OTHER PUBLICATIONS

Bastin, R. J. et al. "Salt Selection and Optimisation Procedures for Pharmaceutical New Chemical Entities" Org. Proc. Res. & Develop. 2000, 4, 427-435.*
Purification of Laboratory Chemicals (PLC), 4th Edn., Elsevier: 1996, Chapter 1.*
Dietzsch, H.-J et al. Pediatrics 1975, 55(1), 96-100.*
John A. Bosso, et al., Efficacy of Aztreonam in Pulmonary Exacerbations of Cystic Fibrosis, *The Pediatr. Infect. Dis. J.*, 6:393-397 (1987).
James L. Cook, M.D., Gram-Negative Bacillary Pneumonia in the Nosocomial Setting, *The American Journal of Medicine,*, 88:3C-34S-37S.
A. Boccazzi, et al., The Pharmacokinetics of Aztreonam and Penetration into the Bronchial Secretions of Critically Ill Patients, *Journal of Antimicrobial Chemotherapy*, 23:401-407 (1989).
Harold C. Neu, M.D., Aztreonam Activity, Pharmacology and Clinical Uses, *The American Journal of Medicine*, 88:3C-2S-3C-6S.
John J. LiPuma, MD, *Burkholderia cepacia*, Management Issues and New Insights, *Clinics in Chest Medicine*, 19/3:473-486 (Sep. 1998).
Stephen C. Aronoff, et al., In Vitro Activities of Aztreonam, Piperacillin, and Ticarcillin Combined with Amikacin Against Amikacin-Resistant *Pseudomonas aeruginosa* and *P. cepacia* Isolates from Children with Cystic Fibrosis, *Antimicrobial Agents and Chemotherapy*, 25/2:279-280 (Feb. 1984).
John A. Bosso, et al., In Vitro Activities of Combinations of Aztreonam, Ciprofloxacin and Ceftazidime Against Clinical Isolates of *Pseudomonas aeruginosa* and *Pseudomonas cepacia* from Patients with Cystic Fibrosis, *Antimicrobial Agents and Chemotherapy*, 34/3:487-488 (Mar. 1990).

(Continued)

*Primary Examiner*—Sreeni Padmanabhan
*Assistant Examiner*—James H. Alstrum-Acevedo
(74) *Attorney, Agent, or Firm*—Hana Verny; Peters Verny, LLP

(57) ABSTRACT

A method and a composition for treatment of pulmonary bacterial infections caused by gram-negative bacteria suitable for treatment of infection caused by *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Stenotrophomonas maltophilia, Alcaligenes xylosoxidans,* and multidrug resistant *Pseudomonas aeruginosa,* using a concentrated formulation of aztreonam lysinate delivered as an aerosol or dry powder formulation.

16 Claims, 3 Drawing Sheets

OTHER PUBLICATIONS

John M. Matssen, et al., The Use of Aztreonam in the Cystic Fibrosis Patient, *Pediatr. Infect. Dis. J.*, 8/9:S117-S119 (1989).

Preston W. Campbell III, MD., et al., Use of Aerosolized Antibiotics in Patients with Cystic Fibrosis, Consensus Conference, pp. 775-789 (Sep. 1999).

Dapena Fernandez J., et al., Inhaled Aztreonam Therapy in Patients with Cystic Fibrosis Colonized with *Pseudomonas aeruginosa*, Spanish Annals on Pediatrics, 40/3 (1994).

Gerald C. Smaldone, et al., Aerosolized Antibiotics: Current and Future, *Respiratory Care*, 45/6:667-675 (Jun. 2000).

Thomas G. O'Riordan, MD, Inhaled Antimicrobial Therapy: From Cystic Fibrosis to the Flue, *Respiratory Care*, 45/7:836-845 (Jul. 2000).

Robert G. Bell, et al., Stability of Intravenous Admixtures of Aztreonam and Cefoxitin, Gentamicin, Metronidazole, or Tobramycin, *American Journal of Hospital Pharmacy*, 43:1444-1453 (Jun. 1986).

Michael J. James, et al, Stability of Intravenous Admixtures of Aztreonam and Ampicillin, *American Journal of Hospital Pharmacy*, 42:1095-1100 (May 1985).

Desppina Daisy Frangolias, et al., *Burkkholderia cepacia* in Cystic Fibrosis, *Am J of Respir Crit Care Med.*, 160:1572-1577 (1999).

Diane H. Johnson, et al., Aztreonam, Medical of Clinics of North America, 79/4:733-743 (Jul. 4, 1995).

Woo, M.S., et al., Use of Aerosolized Aztreonam in CF Lung Transplant Patients Colonized With *Burkholder cepacia*, 2002 Cystic Fibrosis Conference, p. 322:419.

Petra Borsje, MD, et al., Aerosol Therapy in Cysitc Fibrosis: A Survey of 54 CF Centers, *Pediatric Pulmonology*, 30:368-376 (2000).

Rafael Canton, PD, PhD, et al., Lung Colonization with *Enterobacteriaceae* Producing Extended-Spectrum β-Lactamases in Cystic Fibrosis Patients, *Pediatric Pulmonology*, 24:213-217 (1997).

S. Ballestero, et al., *Stenotraphomonas maltophilia* in Cystic Fibrosis Patients, 20th European Cystic Conference, Brussels, Belgium, pp. 18-21 (Jun. 1995).

Sira Carrasco, et al., The General Approach to Cystic Fibrosis Pulmonary Infection in Spain, *Cystic Fibrosis Pulmonary Infections: Lessons From Around The World*, Chapter 18, pp. 223-230 (1996).

Klaus Florey, Aztrenonam, *Analytical Profiles of Drug Substances*, 17:1-39 (1988).

Ajit B. Thakur, et al., Interaction of Metronidazole with Antibiotics Containing the 2-Aminothiazole Moiety, *Pharmaceutical Research*, 8/11:1424-1429 (1991).

S. A. Ranadive, et al., Formation, Isolation and Identification of Oligomers of Aztreonam, *European Journal of Pharmaceutical Sciences*, 3:281-291 (1995).

Brian E. Scully, M.B., et al., Use of Aztreonam in the Treatment of Serious Infections Due to Multiresistant Gram-Negative Organisms Including *Pseudomonas aeruginosa, The American Journal of Medicine*, 78:251-261 (Feb. 1995).

Hiram C. Polk, Jr. MD, et al., Treatment of Pneumonia in Mechanically Ventilated Trauma Patients, *Arch Surg*, 132:1086-1092 (Oct. 1997).

Stephen P. Newman, Ph.D., Aerosol Deposition Considerations in Inhalation Therapy, *Chest*, 88:2, 152S-160S (Aug. 1995).

Gerald C. Smaldone, et al., Aerosolized Antibiotics: Current and Future, *Respiratory Care*, 45/6:667-675 (Jun. 2000).

Thomas G. O'Riordan, MD, Inhaled Antimicrobial Thereapy: From Cystic Fibrosis to the Flu, *Respiratory Care*, 45/7:836-845 (Jul. 2000).

Robert G. Bell, et al., Stability of Intravenous Admixtures of Aztreonam and Cefoxitin, Gentamicin, Metronidazole, or Tobramycin, *American Journal of Hospital Pharmacy*, 43:1444-1453 (Jun. 1986).

Michael J. James, et al., Stability of Intravenous Admixtures of Aztreonam and Ampicillin, *American Journal of Hospital Pharmacy*, 42:1095-1100 (May 1985).

\* cited by examiner

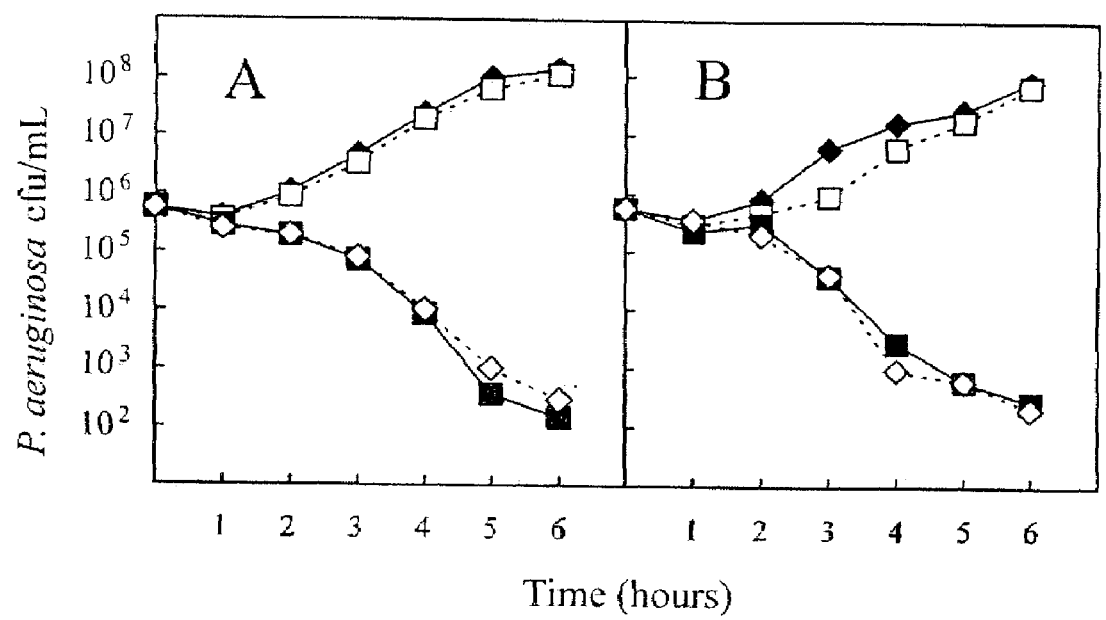

INHALABLE AZTREONAM LYSINATE FORMULATION FOR TREATMENT AND PREVENTION OF PULMONARY BACTERIAL INFECTIONS

This application is a continuation-in-part of U.S. application Ser. No.: 10/027,113 filed on Dec. 20, 2001 (now U.S. Pat. No. 6,660,249) which is based on and claims priority of the Provisional application Ser. No. 60/258,423, filed on Dec. 27, 2000.

BACKGROUND OF THE INVENTION

1. Field of the Invention

The current invention concerns a novel, safe, nonirritating and physiologically compatible inhalable aztreonam lysinate formulation suitable for treatment of pulmonary bacterial infections caused by gram negative bacteria, such as *Escherichia coli, Enterobacteria* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans.* In particular, the invention concerns the inhalable aztreonam lysinate formulation derived from aztreonam alpha form suitable for treatment and prophylaxis of acute and chronic pulmonary bacterial infections, particularly those caused by gram-negative bacteria *Burkholderia cepacia, Stenotrophomonas Maltophilia, Alcaligenes xylosoxidans,* and multidrug resistant *Pseudomonas aeruginosa* which are resistant to treatment with other antibiotics.

The inhalable aztreonam lysinate formulation is delivered as an aerosol or as an inhalable dry powder. For aerosolization, about 1 to about 250 mg of aztreonam lysinate is dissolved in about 1 to about 5 ml of saline or other aqueous solution having a pH between 4.5 and 7.5, delivered to the lung endobronchial space in an aerosol having mass medium average diameter particles predominantly between 1 to 5μ using a nebulizer able to atomize the aztreonam lysinate solution into particles of required sizes. The aerosol formulation has a small volume yet delivers a therapeutically efficacious dose of aztreonam lysinate to the site of the infection in amounts sufficient to treat bacterial pulmonary infections. A combination of the novel formulation with the atomizing nebulizer permits about 50% delivery of the administered dose of aztreonam lysinate into airways. For delivery of dry inhalable powder, aztreonam lysinate is lyophilized, milled or spray dried to particle sizes between about 1 and 5μ. Both the dry powder formulation or a reconstituted aztreonam lysinate solid for aerosolization have a long shelf-life and storage stability.

2. Background and Related Disclosures

A wide variety of gram-negative bacteria cause severe pulmonary infections. Many of these bacteria are or become resistant to commonly used or specialty antibiotics and require treatment with new types of antibiotics. The pulmonary infections caused by gram-negative bacteria are particularly dangerous to patients who have decreased immunoprotective responses, such as, for example, cystic fibrosis and HIV patients, patients with bronchiectasis or those on mechanical ventilation.

Therefore, the bacterial respiratory infections caused by organisms resistant to antibiotics continues to be a major problem, particularly in immunocompromised or hospitalized patients, as well as in patients assisted by mechanical ventilation, as described in *Principles and Practice of Infectious Diseases,* Eds. Mandel, G. L., Bennett, J. E., and Dolin, R., Churchill Livingstone Inc., New York, N.Y., (1995).

Currently accepted therapy for severe bacterial respiratory tract infections, particularly for treatment of pneumonia in patients with underlying illnesses, includes treatment with various intravenous antibacterial agents, often used in two or three way combination. Most of these agents are not suitable, available or FDA approved for either oral or aerosol dosing. In some cases the efficacious systemic intravenous or oral dose, if oral delivery is possible, requires doses which are borderline or outright toxic thus often preventing a use of perfectly good antibiotic for treatment of the pulmonary infections.

Thus it would be desirable to have available other modes of delivery routes of these antibiotics enabling a targeted delivery of smaller amounts of the antibiotic to endobronchial space of airways for treatment of these bacterial infections rather than administering the antibiotic systemically in large amounts.

Additionally, chronically ill patients are often affected with infections caused by bacteria which are largely resistant to commonly used antibiotics or, upon extended use of certain antibiotic, often develop strong resistance to such antibiotic. For example, chronic pulmonary colonization with *Pseudomonas aeruginosa* in patients with cystic fibrosis is a principal cause of their high mortality. When established, the chronic pulmonary infection is very difficult, if not impossible, to eradicate. More than 60% of cystic fibrosis patients are colonized with *Pseudomonas aeruginosa* bacterium strains which are largely resistant to regular and specialty antibiotics, such as piperacillin, ticarcillin, meropenem, netilmicin and only little sensitive to azlocillin, ciprofloxacin, timentin and ceftazidime. Many strains have also been shown to develop resistance to tobramycin and to colistin, if used continuously.

Often, after prolonged antibiotic therapy, a superinfection with organisms intrinsically resistant to oral, intravenous or inhaled antibiotics develops in patients with cystic fibrosis and other chronic pulmonary infections. The four most common drug resistant organisms are *Burkholderia cepacia, Stenotrophomonas maltophilia, Alcaligenes xylosoxidans,* and multidrug resistant *Pseudomonas aeruginosa.*

Cystic fibrosis patients infected with *Burkholderia cepacia* have an increased rate of mortality compared to those patients with *Pseudomonas aeruginosa* infections. In some cystic fibrosis patients, *Burkholderia cepacia* can cause a rapid fatality, as described, for example in *Am. J. Respir. Crit. Care Med.,* 160: 5, 1572–7 (1999).

The high level of antibiotic resistance demonstrated by most strains of *Burkholderia cepacia* severely limits therapeutic options for its treatment (*Clinics Chest Med.,* 19:473–86 (September 1998)). Furthermore, unlike *Pseudomonas aeruginosa, Burkholderia cepacia* can cause epidemic spread among cystic fibrosis patients and therefore any patient infected with *Burkholderia cepacia* is usually isolated from other patients. This causes both additional expenses connected with caring for these patients and may also be psychologically devastating to the patient. Furthermore, most lung transplant centers will not perform a lung transplant on patients infected with *Burkholderia cepacia* (*Clinics Chest Med.,* 19:473–86 (September 1998)). Therefore, the *Burkholderia cepacia* infection is often viewed as a death sentence by patients with cystic fibrosis.

*Burkholderia cepacia* is usually resistant to the parenteral delivery of various antibiotics, including aztreonam lysinate, with showing only 5% of isolates to be sensitive to such treatment (*Antimicrob. Agents Chemother.,* 34: 3, 487–8

(March 1990)). Thus it would be advantageous to have available treatment for *Burkholderia cepacia* infections.

Other gram-negative bacteria intrinsically resistant to tobramycin can also complicate the care of a cystic fibrosis patient. These bacteria include *Stenotrophomonas maltophilia* and *Alcaligenes xylosoxidans*. Antibiotic therapy of these infections is usually also ineffective or leads to rapid emergence of drug resistance. Therefore, the successful treatment of all these infections requires that samples of these isolates are sent to a laboratory for complex antibiotic synergy determination of proper therapy for each individual patient (*Ped. Pulmon.*, S17: 118–119 (1998)). It would, therefore, be also advantageous to provide a therapy for these rare but hard to treat bacterial infections.

Similarly, the development of *P. aeruginosa* infection with strains which are resistant to, that is which have a high minimal inhibitory concentration (MIC) to a majority of antibiotics including tobramycin, predicts declining lung function and also may disqualify the patient from consideration for lung transplant (*Clinics Chest Med.*, 19:535–554 (September 1998)).

Existing antibiotic treatments for *Burkholderia cepacia, Stenotrophomonas maltophilia, Alcaligenes xylosoxidans,* and multidrug resistant *Pseudomonas aeruginosa* pulmonary infections are either ineffective, or lead to rapid emergence of drug resistance.

From the brief description above, it is clear that there is a continuous need for an effective therapy for treatment of acute and chronic pulmonary bacterial infections caused by gram-negative bacteria and particularly those caused by *Burkholderia cepacia, Stenotrophomonas maltophilia, Alcaligenes xylosoxidans,* and multidrug resistant *Pseudomonas aeruginosa* lung infections. Such therapy would preferably comprise an inhalation of the aerosolized drug formulation delivering a therapeutically effective amount of the drug directly to the endobronchial space of airways to avoid systemic treatment.

The problems connected with infections caused with these antibiotic resistant bacteria are very serious and it would be advantageous to have available more efficient modes of treatments with different types of antibiotics.

Aztreonam is a synthetic antibiotic which has a good biological activity against gram-negative bacteria and its arginine salt derived from the beta form has previously been used for intravenous treatment of bacterial infections. However, its use is severely limited due to its low efficacy requiring administration of very large intravenous doses between 1000 and 4000 mg a day in order to treat the infections caused by gram-negative bacteria and also by its salt derivatization which is not suitable for inhalation purposes. Although it would be an antibiotic of choice for complementary treatment of patients treated with tobramycin or other antibiotics, particularly in cystic fibrosis patients, such treatment is not practical because of the high doses required and because of the complication encountered with the arginine salt.

Aztreonam is currently only available as an arginine salt. Arginine has been shown to be toxic to the lung and causes lung tissue irritation, inflammation, bronchospasm and cough and therefore is not suitable for a delivery by aerosolization. Consequently, aztreonam arginine salt is not approved for inhalation use in the United States or elsewhere. However, as the antibiotic for treatment of pulmonary bacterial infections caused by gram negative bacteria, aztreonam could become a drug of choice for such treatment, if it could be delivered by inhalation in therapeutically effective concentrations directly to the lungs and if the problems connected with the aztreonam arginine could be overcome by providing a different, safer and physiologically acceptable salt derivative.

The efficacious administration of aztreonam by inhalation is further complicated by a lack of safe, physiologically acceptable and stable formulations for use by inhalation. Aside from the physiologically acceptable salt, such formulation must meet several criteria, such as certain size range of inhalable particles, certain pH range and certain degree of salinity. When the aerosol contains a large number of particles with a mass medium average diameter (MMAD) larger than 5μ, these are deposited in the upper airways decreasing the amount of antibiotic delivered to the site of infection in the endobronchial space of airways. Similarly, both highly acidic and alkaline or hypotonic or hypertonic conditions lead to respiratory complications, such as bronchospasm and cough, preventing inhalation of the drug.

Thus it would be advantageous and desirable to provide an inhalable formulation for delivery of aztreonam by aerosol or a dry powder formulation for treatment of pulmonary gram-negative bacterial infections and particularly those caused by drug resistant strains *Burkholderia cepacia, Stenotrophomonas maltophilia, Alcaligenes xylosoxidans,* and multidrug resistant *Pseudomonas aeruginosa,* wherein the formulation comprises a smallest possible therapeutically effective amount of drug in a form which does not cause pulmonary inflammation, wherein the pH is adjusted to physiologically acceptable levels, wherein the aqueous solution is isotonic and wherein said formulation has adequate shelf life suitable for commercial distribution, storage and use.

It is, therefore, a primary object of this invention to provide an inhalation aztreonam formulation suitable to efficacious delivery of aztreonam into lung for treatment of pulmonary gram-negative infections, especially those caused by *Burkholderia cepacia, Stenotrophomonas maltophilia, Alcaligenes xylosoxidans,* and multidrug resistant *Pseudomonas aeruginosa* by providing a safe, physiologically acceptable and efficacious formulation for inhalation using a pure concentrated aztreonam lysinate salt, which formulation contains sufficient but not excessive concentration of the aztreonam lysinate, which formulation can be efficiently aerosolized by nebulization using jet, ultrasonic or atomization nebulizers, into an aerosol having particle sizes within a range from 1 to 5μ, or administered as a dry powder, both well tolerated by cystic fibrosis patients and by patients with impaired pulmonary function due to infections, inflammation or another underlying disease.

All patents, patent applications and publications cited herein are hereby incorporated by reference.

SUMMARY

One aspect of this invention is a method for treatment of pulmonary infections caused by gram-negative bacteria by inhalation of aerosolized aztreonam lysinate.

Another aspect of this invention is a method for treatment of pulmonary bacterial infections caused by gram-negative bacteria, said method comprising administration of an inhalable concentrated pure aztreonam lysinate in a dry powder form or as an aerosol containing from about 1 to about 250 mg of aztreonam lysinate, said aztreonam lysinate administered in an inhalable dry powder form or dissolved in from about 1 to about 5 ml of an aerosolable solution of pH between 4.5 and 7.5 containing from about 0.1 to about 0.9% of chloride or other anion to the lung endobronchial space of airways of a patient in need thereof by nebulization in an aerosol having a mass medium average diameter between about 1 and about 5μ, once, twice, three times or four times a day typically up to a daily dose aztreonam lysinate of 500 mg a day but in no instance more than 750 mg a day.

Yet another aspect of this invention is a method for treatment of pulmonary bacterial infections caused by *Escherichia coli, Enterobacteria* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans*, and multidrug resistant *Pseudomonas aeruginosa* using an inhalable formulation of aztreonam lysinate delivered by inhalation to the endobronchial space of airways in a dry powder form or in an aerosol.

Another aspect of this invention is an inhalable pharmaceutically acceptable composition comprising from about 1 to about 250 mg, preferably about 10 to about 150, and most preferably 75 mg per one dose of aztreonam lysinate, said composition suitable for treatment of pulmonary bacterial infections caused by gram-negative bacteria wherein said aztreonam lysinate or the pharmaceutically acceptable salt thereof are prepared as an inhalable dry powder or as an aerosolable solution.

Still another aspect of this invention is an aerosolized aztreonam lysinate formulation comprising from about 25 to about 90 mg/mL, preferably 75 mg/ml of aztreonam lysinate dissolved in from about 1 to 5 ml of a normal or diluted saline or another aqueous solution, having pH between 4.2 and 7.5.

Still another aspect of the current invention is a formulation comprising from about 1 to about 250 mg of aztreonam lysinate in a diluted saline solution ranging from one tenth to a half normal saline or other aqueous solvent containing chloride or another anion, wherein said formulation has a pH between 5.5 and 7.0 and is delivered by aerosolization in about 1–5 ml of solution wherein aerosol has particles of the mass medium average diameter predominantly between 1 and 5μ, wherein said formulation is nebulized using a jet, atomizing, electronic or ultrasonic nebulizer.

Still yet another aspect of the current invention is a dry powder formulation comprising from about 1 to 200 mg of alpha form of aztreonam lysinate, wherein said formulation is lyophilized, milled, spray dried or precipitated into a fine powder having particles with the mass medium average diameter between 1 and 5μ used for inhalation of the dry powder administered from one to four times per day not exceeding 750 mg per day.

Another aspect of this invention is a two-part reconstitution system comprising an aztreonam lysinate in dry or lyophilized powder form and a diluent stored separately until use.

Still another aspect of this invention is a process for preparation of aztreonam lysinate from the alpha form of aztreonate wherein the resulting aztreonam lysinate has a better stability, higher purity and better yield.

BRIEF DESCRIPTION OF FIGURES

FIG. 1 shows aztreonam lysinate activity against *P. aeruginosa* in the absence (FIG. 1A) or presence (FIG. 1B) of hog gastric mucin. Aztreonam lysinate was added to yield a final concentration in the following multiples of the MIC: 0.0 (◆); 0.1 (□) ; 1.0 (■); and 10 (◇). FIG. 1A, no added mucin; FIG. 1B, 10% mucin added.

FIG. 2 shows aztreonam lysinate activity against *P. aeruginosa* in the presence or absence of cystic fibrosis (CF) sputum. Aztreonam lysinate was added to yield a final concentration in the following multiples of the MIC: 0.0 (◆); 0.1 (□); 1.0 (■); and 10 (◇). FIG. 2A, no added sputum; FIG. 2B, 1% sputum added.

FIG. 3 shows tobramycin activity against *P. aeruginosa* in the presence or absence of added mucin. Tobramycin was added to yield a final concentration in the following multiples of the MIC: 0.0 (◆); 1.0 (□); and 10 (■) FIG. 3A, no added mucin; FIG. 3B, 10% mucin added.

DEFINITIONS

Figures 1A, 1B:
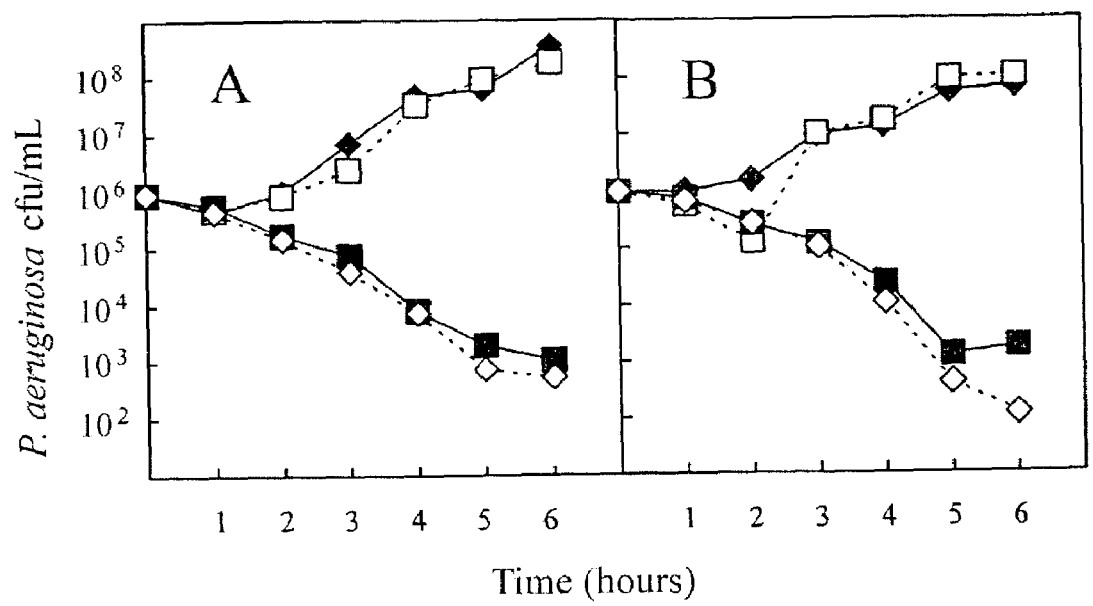

As used herein:

"MMAD" means mass medium average diameter.

"Normal saline" means water solution containing 0.9% (w/v) NaCl.

"Diluted saline" means normal saline containing 0.9% (w/v) NaCl diluted into its lesser strength from about 0.1% to about 0.8%.

"Half normal saline" or "½ NS" means normal saline diluted to its half strength containing 0.45% (w/v) NaCl.

"Quarter normal saline" or "¼ NS" means normal saline diluted to its quarter strength containing 0.225% (w/v) NaCl.

"One tenth normal saline" or "⅒ NS" means normal saline diluted to its one tenth strength containing 0.09% (w/v) NaCl.

"CF" means cystic fibrosis.

"Predominantly" means including at least 70% but preferably 90% of particle sizes between 1 and 5μ.

"Physiologically acceptable solution" means a saline diluted to between ⅒ NS or 1 NS or another aqueous solution comprising from about 31 to about 154 mM of chloride or an equivalent concentration of bromine or iodine.

"Composition" means an aztreonam lysinate containing formulation additionally containing other components, such as excipients, diluents, isotonic solutions, buffers, etc.

"Formulation" means a specific composition formulated for specific use, such as for aerosolization of aztreonam lysinate containing solution or nebulization of dry powder.

"Aztreonam lysinate composition" or "aztreonam lysinate formulation" means a composition or formulation comprising an indicated amount of aztreonam lysinate salt. Thus, if for example, the dose of aztreonam lysinate comprises molar amount of aztreonam free base it contains 1.8 multiple molar amount of lysine.

"Concentrated aztreonam lysinate" means an aztreonam lysinate concentrated into a form which permits dilution of, or more than, 75 mg of aztreonam lysinate in 1 ml of diluent.

"Alpha form of aztreonam" means an alpha sterochemical configuration of aztreonam. The alpha form of aztreonam is distinguishable from the beta, gamma and delta forms of aztreonam. Each form seems to have different chemical and physical properties, such as, for example, stability, crystallization point and diffraction curve. Differences between these two forms are described, for example in U.S. Pat. No. 4,946,838. Alpha or beta aztreonam arginine salt are described in EP application 0 297 580 B1. Alpha, beta, gamma and delta forms of aztreonam and their chemical and physical properties are described in U.S. Pat. No. 4,826,973. All the above cited patents are herein incorporated by reference.

DETAILED DESCRIPTION OF THE INVENTION

The current invention concerns a discovery that a specifically formulated inhalable aztreonam lysinate is efficacious for treatment of pulmonary infections caused by gram-negative bacteria.

Consequently, the invention concerns an inhalable composition and a method of treatment for pulmonary bacterial infections caused by *Escherichia coli, Enterobacter* species, *Klebsiella pneumoniae, Klebsiella oxytoca, Proteus mirabilis, Pseudomonas aeruginosa, Serratia marcescens, Haemophilus influenzae*, including ampicillin-resistant and other penicillinases-producing strains and *Nitrobacter* species as well as for treatment of more rare bacteria, such as *Burkholderia cepacia, Stenotrophomonas maltophilia, Alcaligenes xylosoxidans,* and multidrug resistant *Pseudomonas aeruginosa*. The aztreonam lysinate formulation is delivered to a patient's endobronchial space of airways by inhalation of a dry powder or an aerosol solution.

The method of treatment of pulmonary bacterial infections is especially suitable for treatment of patients with cystic fibrosis, bronchiectasis and patients with pneumonia assisted by ventilators, however it is also useful for treatment of other conditions that are complicated by infections caused by *Burkholderia cepacia, Stenotrophomonas maltophilia, Alcaligenes xylosoxidans,* and multidrug resistant *Pseudomonas aeruginosa* or other gram-negative bacteria.

The current invention thus concerns a novel, efficacious, safe, nonirritating and physiologically compatible inhalable aztreonam lysinate composition suitable for treatment of pulmonary bacterial infections caused by gram-negative bacteria particularly those which are resistant to treatment with other antibiotics. The inhalable formulation of aztreonam lysinate is suitable both for treatment and prophylaxis of acute and chronic pulmonary infections. The inhalable formulation is delivered as an aerosol or as an inhalable dry powder. For aerosolization, aztreonam lysinate is dissolved in a minimal volume of about 1 to about 5 ml of an aqueous solvent comprising chloride bromine or iodine ion, having a pH between 4.2 and 7.5, delivered to the endobronchial space in an aerosol having mass medium average diameter particles predominantly between 1 to 5μ using a nebulizer able to aerosolize the aztreonam lysinate solution into particles of required sizes.

In another aspect, the current invention also concerns finding that the aztreonam lysinate derived from the alpha form of aztreonam, as compared to the beta form, has better properties and are more suited for preparation of aztreonam lysinate salt for inhalable product. The use of the alpha form for preparation of aztreonam lysinate provides demonstrable advantages in both manufacturing processes and results in the product with higher purity and better stability.

This aspect is novel in that until now, the alpha form of aztreonam was described as unstable and its conversion to beta form of aztreonam was required for preparation of therapeutic agents. The findings described herein are related to processes connected with formation of the aztreonam lysinate salt.

I. Aztreonam Generally

Aztreonam is a compound known under its chemical name (Z)-2-[[[(2-amino-4-thiazolyl)[[(2S,3S)-2-methyl-4-oxo-1-sulfo-3-azetidinyl]carbamoyl]methylene]amino]oxy]-2-methylpropionic acid.

Aztreonam is a known synthetic antibiotic with antibacterial activity against most gram-negative bacteria. Aztreonam is a monobactam and as such it has a unique monocyclic beta-lactam nucleus, and is therefore structurally different from other β-lactam antibiotics such as, for example penicillins, cephalosporins, or cephamycins. The sulfonic acid substituent in the 1-position of the ring activates the beta-lactam moiety. An aminothiazolyl oxime side chain in the 3-position and a methyl group in the 4-position confer the specific antibacterial spectrum and beta-lactamase stability.

Aztreonam is chemically known and available as alpha, beta, gamma and delta forms. Aztreonam arginine salt, known under its trade name AZACTAM® is derived from the beta form.

AZACTAM® (aztreonam arginine for injection, USP) commercially available from DURA Pharmaceuticals, Inc., San Diego, Calif., contains aztreonam as the active ingredient. AZACTAM is formulated as arginine salt and is currently FDA approved only for intramuscular or intravenous use (*PDR*, pg. 1159 (2001)).

A. Disadvantages of Aztreonam Arginine Salt

The commercially available AZACTAM for intravenous or intramuscular formulation is not suitable for inhalable use because of the presence of arginine in the formulation. Arginine has been found to cause pulmonary inflammation when administered in an aerosol form to the lung in the rat.

Arginine has been unsuccessfully used as a potential aerosolized mucolytic agent in cystic fibrosis patients. A study, described in *Pediatrics,* 55:96–100 (1975) recommends that arginine should not be used in cystic fibrosis patients. In a study of 24 patients with cystic fibrosis, inhalation therapy with an arginine solution in five patients had to be stopped because of the inflammation confirmed by bronchoscopy, cough and severe deterioration of their general conditions. Later, arginine was identified as a substrate for the production of nitric oxide radicals which are known to cause the lung inflammation, bronchospasm and irritation.

Nitric oxide radical reacts with the superoxide anion to form peronitrile, which is by itself toxic to the tissue and also may further react to form highly reactive and toxic hydroxyl radical. Since inflammation is a serious impairment for cystic fibrosis and all other diseases which this invention attempts to treat, use of arginine salt is not suitable as it would defeat this purpose and worsen rather than improve the patient conditions.

Arginine is also an important substrate for immune complex injury in the lung, as disclosed in *PNAS,* 14:6338–6342 (1991). Since the aerosolization concentrates high levels of the aerosolized drug in the lung as compared to dilution seen after intravenous administration, the aerosolization of the aztreonam arginine salt would be detrimental rather than advantageous for treatment of cystic fibrosis patients or patients suffering from pulmonary infections. Moreover, it would dilute and/or negate the effect of aztreonam.

Aztreonam, in any form, is not currently approved or used for inhalation treatment and aerosol administration in the United States. Consequently, there is no known aztreonam or aztreonam lysinate containing formulation available for aerosol delivery to the endobronchial space of airways.

The only attempt to deliver aztreonam arginine intermittently to cystic fibrosis subjects is described in *Spanish Annals on Pediatrics,* 40: No.3 (1994) where such delivery was made in an open label trial in cystic fibrosis patients with intermittently administered 500 and 1000 mg of AZACTAM USP arginine salt, twice a day for 21 days, using CR60 System 22 unit nebulizer. The intent of this study was to treat aztreonam sensitive *Pseudomonas aeruginosa* organisms, but not multidrug resistant *Pseudomonas aeruginosa*. No effort or speculation was to treat *Burkhold-* eria cepacia, Stenotrophomonas maltophilia, infections caused by Alcaligenes xylosoxidans or other gram-negative bacteria.

In this study, the nebulized solution of aztreonam was delivered after the physical therapy session. Prior to the therapy session, the patients were administered 3 cc of saline alone or mixed with bronchodilators salbutamol or ipratropium bromide and fenoterol bromohidrate to prevent bronchospasm. The treatment described in this study thus required both the pretreatment with inhaled saline and/or bronchodilating agents and prior physical therapy session as well as administration of large doses of the drug to be administered twice a day. Although in about 80% of patients lung function has somehow improved, such improvement was not statistically significant. At least one patient could not tolerate the therapy due to bronchospasm. Most patients required administration of bronchodilators and all patients underwent physical therapy prior to aztreonam treatment in order to tolerate the administration of large doses of nebulized aztreonam. Aztreonam therapy was discontinued if in vitro resistance was found. One patient developed *Burkholderia cepacia*, which was viewed as superinfection, and a possible adverse outcome. The reference, although suggestive of efficacy in drug sensitive *Pseudomonas aeruginosa*, which is expected because the drug is known for its effect on the gram-negative bacteria, does not disclose the use of aztreonam, aztreonam lysinate, alpha form of aztreonam, its continuous use or the use of aztreonam or aztreonam lysinate for treatment of multidrug resistant *P. aeruginosa* and teaches away from use in *Burkholderia cepacia, Stenotrophomonas maltophilia, Alcaligenes xylosoxidans,* and multidrug resistant *Pseudomonas aeruginosa* infections. Furthermore, the high incidence of bronchospasm developed with use of the published formula requiring either discontinuation or pretreatment with bronchodilators indicates the need for a different formulation safe for inhalation use.

As discussed above, currently the only commercially available salt of aztreonam is arginine and, as also already discussed above, the aztreonam arginine salt is not suitable for inhalation administration because arginine, after aerosol exposure, is known to cause pulmonary inflammation, bronchospasm and cough. AZACTAM, aztreonam containing arginine salt, is not approved by regulatory authorities for inhalation use. Therefore, another aztreonam salt is needed to achieve a safe formulation of aztreonam for inhalation treatment of patients with pulmonary infections or those having impaired pulmonary function due to cystic fibrosis or bronchiectasis.

Since the aztreonam containing arginine is not suitable for inhalation according to this invention, other acid addition salts were prepared and tested. Aztreonam lysinate, particularly aztreonam lysinate derived from aztreonam alpha form, was found to be pharmacologically most acceptable for inhalation purposes when administered as a dry powder or aerosol without causing any undesirable reactions.

The preferred pharmaceutically acceptable aztreonam lysinate salt is derived from reaction of aztreonam or alpha aztreonam with lysine.

B. Alpha and Beta Aztreonam

Previously, a preparation of aztreonam arginine and other salts but no lysinate involved almost exclusively the beta form of aztreonam. Alpha form of aztreonam was previously thought to be unstable and unusable for preparation of therapeutic compositions. Beta form of aztreonam was considered to be the stable form and if the alpha form was used it was thought to be necessary to first convert the alpha form to the beta form of aztreonam.

The U.S. Pat. No. 4,946,838 presents conclusive evidence that the alpha form of aztreonam is unstable and before used for preparation of any therapeutic product it should be converted to the beta form of aztreonam. The EPO application EP 0 297 580 B1 describes preparation of aztreonam arginine salt derived from alpha or beta aztreonam. Other disclosed salts are sodium carbonate, sodium bicarbonate, sodium citrate, sodium phosphate and sodium hydroxide. The European Patent application thus discloses the use of amorphous, pharmaceutically acceptable aztreonam salts, specifically limited to arginine, sodium carbonate, sodium bicarbonate, sodium citrate, sodium phosphate, and sodium hydroxide. Aztreonam salt described therein is being prepared by lyophilization for parenteral use. Specifically, the application identifies alpha or beta form mixed with arginine or another salt in dry state and then mixed with water to bring the pH to 5.0. The application does not disclose the use of aztreonam for aerosol use or as the lysine salt.

Aztreonam can exist in anhydrous amorphous and crystalline forms and also in hydrated and solvated crystalline forms. The amorphous and hydrated forms interconvert under certain temperature and humidity conditions and are both unstable. The anhydrous crystalline and solvated forms show good stability and have not shown interconversion in the solid state. However in the presence of excipients that release moisture, the anhydrous crystalline form decomposes to an extent dependent on moisture content and temperature.

According to the prior art, the crystalline form of alpha form of aztreonam is considered to be unstable and must be converted to the beta form by recrystallization from ethanol. Following this recrystallization step, the beta form is considered to be very stable. However, the re-crystallized aztreonam contains 1–2% of residual organic solvent, typically ethanol.

Stability of the alpha or beta compound is determined by its loss at various temperatures. Thus, the prior art reports that after one week of storage alpha form experiences approximately 1% loss at room temperature and an 80% loss at 80° C. In contrast, the beta form, which after a 12 month storage at 5% to 75% relative humidity and at −20° C. to 40° C. was more stable. Under these range of conditions, the samples were found to have undergone slight increase (<2%) in impurity level by TLC method, and a drop of 3.0 to 3.5% in potency, as determined by HPLC.

In the process of developing this invention it was unexpectedly found that for preparation of a lyophilized form of aztreonam lysinate for aerosol an alpha form of aztreonam, previously thought to be unstable, was actually the preferred form for the starting material for the lysine salt conversion process.

When compared to the beta material, the alpha material was found to have fewer impurities. The type and degree of impurities in the inhalation formulation are important for and have specific impact on the long term stability of the drug and shelf-life of the final product. The beta form of aztreonam is manufactured from the alpha form using an ethanol re-crystallization process that results in 5000–10, 000 ppm residual ethanol. USP for FDA limits is <5000 ppm. Over time, this presence of ethanol leads to the generation of an ethyl ester, an impurity, which is not present in the alpha form.

Additionally, the beta form of aztreonam is relatively insoluble in water and clumps during dissolution to make the lysine salt. This results in the formation of open-chain nucleophilic ring opening and results in an undesirable added impurity. Under the presence of moisture the open chain can grow under various temperature and humidity conditions, leading to higher instability. Testing data shows the initial impurity levels generated from the beta form is in the 1% range, close to the FDA limit for the permissible impurity while the impurity levels of aztreonam lysinate generated from alpha form is less than 0.1%.

C. Aztreonam Lysinate

Aztreonam lysinate subject of this invention is derived preferentially from alpha aztreonam form, however, it can also be derived from other aztreonam forms. At this time, aztreonam lysinate, derived either from the alpha, beta, gamma or from another aztreonam form is not known and was never before described. The lysine salt of generic β-lactams but not aztreonam specifically is described in U.S. Pat. No. 4,550,105.

The production of aztreonam lysinate derived from alpha aztreonam form without converting the alpha form into the beta form is a novel process not disclosed or suggested by any prior art.

The current novel method for preparation of aztreonam for inhalation is based on the finding that the alpha form of aztreonam, when solubilized in water and stirred, forms an emulsion or smooth slurry and when a lysine salt solution is titrated to the mixture, results in a rapid formation of an amorphous lysine salt. This salt has similar stability characteristics to the lyophilized beta form, however, when the alpha derived lysinate is dried it does not cause the opening of the ring and thus the initial impurity levels generated from the alpha form is less than 0.1–1%, substantially less than FDA limit for the impurity.

Therefore, by using the alpha form of aztreonam, the final product contains much lower initial impurity levels, with higher stability and less degradation over time that leads to a product with a longer shelf life. In the current process for preparation aztreonam lysinate from alpha form, the basic salt conversion volumes, ratio of individual components and pH of the reaction mixture is titrated to a fixed level. Manufacturing of the product using the titration process of the invention confirms finding of less than 100 ppm of residual ethanol in the alpha form aztreonam lysinate compared to the beta form wherein the residual ethanol levels were up to 10,000 ppm in the same volume. By using the alpha form, the formation of ethyl ester, another impurity detected in the beta aztreonam forms is eliminated. Concerning the stability of the two formulations, the accelerated stability method shows that the beta form degrades from the initial 0.9% open chain to over 2% at 30 days whereas for alpha form an initial 0.06% open chain grows only to 1.2% after 90 days under the same testing conditions.

The prior art dealing with alpha and beta aztreonam involves conversion of the alpha form to the beta form. Such conversion step, if used for production of aztreonam lysinate necessarily involves combining the beta form of the aztreonam, having a pH of approximately 2.3, with the lysine component, having a pH of approximately 10, to yield the aztreonam lysinate as a final product. The addition of a lysine component to the beta form of the aztreonam creates excessive ion exchange in the titration of the aztreonam acid to a physiologically acceptable pH. Additionally, this reaction results in an undesirable side reaction with open chain formation of the beta lactam ring in the aztreonam further leading to the final product having a higher degree of impurity, instability and an undesirably high osmolality. Albeit, while the alpha form of aztreonam is preferred, the beta form aztreonam lysinate is also intended to be within the scope of this invention.

High osmolality is not a desirable property of the aztreonam for inhalation as will be described in greater detail below, as the inhalable aztreonam formulation requires very specific degree and range of osmolality (Section III. A4 and priority document Ser. No. 10/027,113). High osmolality may cause the patient to react to the inhalation with bronchospasm or cough.

Use of the alpha form of aztreonam and preparation of the lysinated salt using the current process produces a more stable product with a better pH profile, lower impurity content, longer stability and a desirably reduced osmolality.

Three potential techniques were developed to yield the aztreonam lysinate derived from the alpha form of aztreonam. All these techniques avoid conversion to the beta form. The first techniques involves titration of lysine salt into the alpha form of aztreonam. The second techniques involves vacuum-drying of the raw alpha aztreonam at the end point of the synthesis when the aztreonam is combined with lysine in a lyophilizer and the final aztreonam lysinate is produced directly. The third technique involves spray-drying of the alpha form of the aztreonam with lysine into a bulk solid, to produce the aztreonam lysinate as the final product without need of going through the conversion to the beta form.

As already discussed above, the use of the aztreonam beta form for production of aztreonam arginine requires an amount of ethanol solvent in quantities that cannot be readily removed. Such residual solvent leads to formation of an ethyl ester in the aztreonam product during the first few months of storage and leads to an impure final product having a lesser stability as well as the shorter shelf-life of the product.

The current preferred process for preparation of the aztreonam lysinate derived from alpha form thus comprises solubilization of alpha form of aztreonam in water and subsequent titration of an aqueous solution of solid form of lysine into the aztreonam to form the lysine salt. The mixture is then lyophilized or spray dried. The current process avoids cleavage of the beta lactam ring by advantageously employing a titration to achieve a desirable pH profile of the aztreonam lysinate which is contrary to the techniques used for beta aztreonam salt preparation which comprises combination of the dry powder of beta aztreonam with L-arginine in a mixture, followed by solubilization of the powder with water and titration to a final concentration.

In either of the techniques disclosed herein for preparation of the aztreonam lysinate derived from the alpha form of aztreonam, conversion to the beta form as well as all problems connected with production of the aztreonam derived from the beta form of aztreonam is avoided.

D. Aztreonam Lysinate Pharmacological Activity

Aztreonam lysinate exhibits potent and specific activity in vitro against a wide spectrum of gram-negative aerobic pathogens including *Pseudomonas aeruginosa*. The bactericidal action of aztreonam lysinate results from the inhibition of bacterial cell wall synthesis due to a high affinity of aztreonam lysinate for penicillin binding protein 3 (PBP3).

Aztreonam lysinate, unlike the majority of β-lactam antibiotics, does not induce β-lactamase activity and its molecular structure confers a high degree of resistance to hydrolysis by β-lactamases, such as penicillinases and cephalosporinases, produced by most gram-negative and gram-positive pathogens. Aztreonam lysinate is therefore especially effective against gram-negative aerobic organisms that are resistant to antibiotics hydrolyzed by β-lactamases.

Aztreonam lysinate maintains its antimicrobial activity at a pH ranging from 6 to 8 in vitro as well as in the presence of human serum and under anaerobic conditions. Aztreonam lysinate is active in vitro and is effective in laboratory animal models and clinical infections against most strains of the following organisms, *Escherichia coli, Enterobacter* species, *Klebsiella pneumoniae, Klebsiella oxytoca, Proteus mirabilis, Pseudomonas aeruginosa, Serratia marcescens, Haemophilus influenzae,* and *Nitrobacter* species, including many that are multi-resistant to other antibiotics such as certain cephalosporins, penicillins, and aminoglycosides.

Currently, the only infections for which aztreonam arginine salt is FDA approved are those caused by *Escherichia coli, Klebsiella pneumoniae, Pseudomonas aeruginosa, Haemophilus influenzae, Proteus mirabilis, Enterobacter* species and *Serratia marcescens.*

It has now been discovered that, all the above named bacterial strains as well as rare and highly resistant strains, such as *Burkholderia cepacia, Stenotrophomonas maltophilia, Alcaligenes xylosoxidans,* and multidrug resistant *Pseudomonas aeruginosa* are successfully eradicated by daily treatment with low doses between about 1 and about 250 mg, preferably about 75 mg/mL, of aztreonam lysinate, preferably administered once or twice a day, with total daily doses not exceeding 750 mg/day.

II. Aztreonam Lysinate Inhalable Composition

The current invention primarily concerns a concentrated inhalable aztreonam lysinate composition suitable for efficacious delivery of aztreonam lysinate into the endobronchial space of airways by aerosolization or as a dry powder.

The invention is most preferably suitable for formulation of concentrated aztreonam lysinate for aerosolization by atomizing, jet, ultrasonic, pressurized, vibrating porous plate or equivalent nebulizers or by dry powder inhalers which predominantly produce aztreonam lysinate aerosol or dry powder particles between 1 and 5μ. Such particle sizes are necessary for efficacious delivery of aztreonam lysinate into the endobronchial space to treat bacterial infections.

A. Aerosolized Aztreonam Lysinate Composition

Aztreonam lysinate composition for aerosolization is formulated for efficacious delivery of aerosolized aztreonam lysinate to the lung endobronchial space of airways.

The aerosol formulation is delivered in a total volume of between about 1 and about 5 ml of aqueous physiologically acceptable solution for one inhalation dose. When formulated and delivered according to the method of invention, it delivers a therapeutically efficacious dose of aztreonam lysinate to the site of the infection in amount sufficient to treat bacterial pulmonary infections.

A combination of the novel aqueous formulation with the atomizing, jet, pressurized, vibrating porous plate or ultrasonic nebulizer permits, depending on the nebulizer, about at least 20 to about 90%, typically about 70% delivery of the administered dose of aztreonam lysinate into airways.

The formulation contains a minimal yet efficacious amount of aztreonam lysinate from about 1 to about 250 mg, more preferably from about 25 to about 90 mg/mL, and most preferably about 75 mg/mL, formulated in the smallest possible volume of physiologically acceptable diluent having a certain degree of salinity and certain pH, adjusted to permit generation of an aztreonam lysinate aerosol well tolerated by patients but minimizing the development of secondary undesirable side effects such as bronchospasm and cough.

Primary requirements for aerosolized aztreonam lysinate formulation are its safety and efficacy. Additional advantages are lower cost, manufacturing convenience, purity of the product, practicality of use, long shelf-life, storage and manipulation of the aerosol device. These requirements for aerosolized aztreonam lysinate have now been found to be met by the formulation containing certain degree of salinity and have certain pH range.

A. Dosage of Aztreonam Lysinate

Aztreonam lysinate has a relatively short life-time. Its half life time is about 1–2 hours and within ten to twelve hours the whole aztreonam dose is eliminated. Consequently, the effective treatment of bacterial pulmonary infections requires a treatment regimen which provides sufficient amount of drug to maintain the antibacterial level of aztreonam lysinate in the lung. Such regimen thus requires administration of an inhalable aztreonam lysinate one to several, preferably two to four, times a day. Most preferred dosing regimen for patient convenience is once or twice a day, however, because of a specific effect aztreonam lysinate asserts on the bacteria, and because of its relatively short life-time of about 12 hours, more than twice a day dosing is often required for complete eradication of the bacteria from the endobronchial space.

It is therefore preferable to deliver aerosolized or dry powder aztreonam lysinate in a smallest therapeutically efficacious amount at least twice a day, in some instances three to four times, and exceptionally more than four times a day. A dose of aztreonam lysinate or a salt thereof is therefor set to be between 1 and 250 mg per one dose formulated in, most preferably, about 75 mg of aztreonam/mL.

Typically, one therapeutically effective dose contains between 1 and 250 mg, preferably between 25 to 90 mg of aztreonam lysinate, in equivalent, administered by means that provides at least about 50%–70% efficacy of aztreonam lysinate delivery to the endobronchial space. Thus, with about a 250 mg dose, 125 mg of aztreonam lysinate is delivered during each administration. 100–250 mg of aztreonam lysinate delivered to the lung has been found to be efficacious in eradication of bacteria. In no instance should one dose exceed 250 mg. Above this amount, aerosolization is difficult, the drug tends to precipitate, and larger volumes are necessary for its delivery by aerosol, which defeats the purpose of the invention to deliver the therapeutical amount of drug with the greatest efficiency.

Determination of effective dosage of administered aztreonam lysinate and the regimen used for treatment of each patient depends on the responsiveness of the individual patient to the treatment. The ultimate decisive factor is the expected level of aztreonam lysinate in the sputum after aerosolization. The optimal range of aztreonam lysinate in 1 ml of sputum at any given time should be in the 500 to 2000 μg/mL range. Thus, the frequency of the administration is correlated with the effectiveness of administered aztreonam lysinate.

The effectiveness of aerosolized aztreonam lysinate is surprisingly high when compared to effectiveness of the intravenously administered aztreonam lysinate where the serum peak levels following the maximum permitted dose 2,000 mg resulted only in 242 ug/mL of sputum. Following such intravenous administration, the 6 hours levels were found to be in the range of 16 ug/ml, which is the MIC for non-resistant *Pseudomonas aeruginosa.*

The new mode of administration permitting a noninvasive administration of small yet effective amounts of aztreonam lysinate directly into lungs is a great improvement compared to all previously known method used for delivery of aztreonam lysinate.

2. Effect of pH on Aztreonam Lysinate Formulation

The solution or diluent used for preparation of aztreonam lysinate aerosol has a limited pH range from 4.2 to 7.5, preferably between 5.5 and 7.0.

The pH of the formulation is an important feature for aerosolized aztreonam lysinate delivery. When the aerosol is either acidic or basic, it can cause bronchospasm and cough. Although the safe range of pH is relative and some patients may tolerate a mildly acidic aerosol, others, particularly those with cystic fibrosis or other underlying disease will experience bronchospasm. Any aerosol with a pH of less than 4.5 typically induces bronchospasm. Aerosols with a pH between 4.5 and 5.5 will cause bronchospasm occasionally. Testing with aztreonam lysinate aerosol discovered that an aerosblizable aztreonam lysinate formulation having a pH between 5.5 and 7.0 is well tolerated and safe. Any aerosol having pH greater than 7.5 is to be avoided as the body tissues are unable to buffer alkaline aerosols. Aerosol with controlled pH below 4.5 and over 7.5 causes lung irritation accompanied by severe bronchospasm, cough and inflammatory reactions.

For these reasons as well as for the avoidance of bronchospasm cough or inflammation in patients, the optimum pH for the aerosol formulation was determined to be between pH 5.5 to pH 7.0.

Consequently, the aztreonam lysinate aerosol formulation is adjusted to pH between 4.5 and 7.5 with preferred pH range from about 5.5 to 7.0. Most preferred pH range is from 5.5 to 6.5.

3. Effect of Salinity on the Aztreonam Lysinate Formulation

Patients suffering from acute or chronic endobronchial infections and particularly those with cystic fibrosis or bronchiectasis have increased sensitivity to various chemical agents and have high incidence of bronchospastic, asthmatic or cough incidents. Their airways are particularly sensitive to hypotonic or hypertonic and acidic or alkaline conditions and to the presence of any permanent ion, such as chloride. Any imbalance in these conditions or the absence of chloride below certain values leads to bronchospastic or inflammatory events and/or cough which greatly impair treatment with inhalable formulations. Both these conditions prevent efficient delivery of aerosolized aztreonam lysinate into the endobronchial space. The clinical manifestations of the irritated airways are extremely undesirable.

Clearly, for aztreonam lysinate, it is not possible to use solely an aqueous solvent without providing certain degree of osmolality to meet and emulate physiological conditions found in healthy lungs. Consequently, certain amount of the chloride or another anion is needed for successful and efficacious delivery of aerosolized aztreonam lysinate but such amount is much lower than amounts provided and typically used for aerosols of other compounds.

Bronchospasm or cough reflexes do not respond to the same osmolality of the diluent for aerosolization, however, they can be sufficiently controlled and/or suppressed when the osmolality of the diluent is in a certain range. Preferred solution for nebulization of aztreonam lysinate which is safe and has airways tolerance has a total osmolality between 50 and 550 mOsm/kg with a range of chloride concentration of between 31 mM and 300 mM. The given osmolality controls bronchospasm, the chloride concentration, as a permeant anion, controls cough. In this regard the chloride anion can be substituted with bromine or iodine anions, since both are permeant anions. In addition, bicarbonate may be wholly or partially substituted for chloride ion. Normal saline (NS) contains 154 mM of chloride whereas 31 mM of chloride corresponds to about 0.2 normal saline.

Consequently, the formulation for aztreonam lysinate aerosol of the invention comprises from about 1 to about 90 mg, preferably about 75 mg, of aztreonam lysinate dissolved in 1 ml of a normal, or preferably a diluted saline to from about 1/10 normal saline (NS) to about and at most to 1 NS solution, preferably from about 1/10 to about 1/4 NS, that is a one tenth to one quarter diluted normal saline. It has now been discovered that aztreonam lysinate is efficaciously delivered into lungs when dissolved in lesser than normal saline, that is saline containing 0.9% of sodium chloride, and that the concentration of a chloride ion equal to or lesser than 1/4 N saline permits and assures a delivery of aztreonam lysinate into endobronchial space.

The aztreonam lysinate formulation containing about 50 mg of aztreonam lysinate per 1 ml of 0.2 NS has an osmolality of about 290 mOsm/l. Such osmolality is within a safe range of aerosols suitable for administration to patients suffering from pulmonary bacterial infections and also those patients with a cystic fibrosis or bronchiectasis.

An additional feature and advantage of using 1/10 to 1/4 NS solution comprising 50 mg/ml aztreonam lysinate is that the resulting aerosol formulation is very efficiently nebulized by an atomic, jet or ultrasonic nebulizer compared to aztreonam lysinate dissolved in a normal saline. Since the delivery of aztreonam lysinate formulated as described herein is much more efficient, much lower amount of aztreonam lysinate is needed to achieve complete eradication of gram-negative bacteria in lungs. Instead of 1000 to 4000 mg of aztreonam which was shown to be somehow effective in the only one prior attempt to aerosolize aztreonam, the formulation of aztreonam lysinate according to this invention permits treatments with as little as 1 mg/ml and with at most up to 50 mg/ml of aztreonam lysinate in a maximum amount of 5 ml volume, delivered preferably with an atomizing, jet, electronic or ultrasonic nebulizer.

4. Aerosolizable Aztreonam Lysinate Formulation

The aztreonam lysinate aerosolizable formulation comprises from about 1 to about 250 mg, preferably formulated in about 25 to about 90 mg/ml, most preferably about 75 mg/mL of aztreonam lysinate dissolved in about 1 to 5 ml of an aqueous solution containing low concentration of chloride ion between 0.09% and 0.9%, having pH adjusted to between 4.2 and 7.5, said formulation delivered by aerosolization using an atomizing, jet, electronic, ultrasonic nebulizer.

The most preferred aerosol formulation for aztreonam lysinate comprises 75 mg/mL of aztreonam lysinate dissolved in about 1–5 ml of a saline diluted preferably to a quarter (0.225%) or one tenth (0.09%) strength of normal saline, having pH adjusted to between 5.5 and 7.0, delivered by nebulization in aerosol particles having the mass medium average diameter predominantly between 1 and 5μ, wherein said formulation is nebulized using an atomizing, jet, electronic or ultrasonic nebulizer. Dose of aztreonam is recalculated to refer only to an aztreonam component.

Using the PARI E-flow nebulizer commercially available from PARI, Starnberg Germany, the delivery time for one ml of 75 mg/mL aztreonam lysinate solution is 3 minutes compared to 4 minutes for the 90 mg/mL aztreonam lysinate solution. The delivery is 25 mg aztreonam per minute is faster for the 75 mg/mL than the delivery of 22.5 mg aztreonam per minute for the 90 mg/mL solution. Since time of delivery is important from a patient perspective and improves compliance, the discovery that 75 mg/mL formulation is delivered faster than the 90 mg/mL is important as well as unexpected. The 90 mg/mL is the maximum concentration of aztreonam lysinate that can be dissolved in 1 ml of the solution.

It was further discovered that the highest dissolvable concentration, i.e. 90 mg/mL, is not as well nebulizable as the 75 mg/mL concentration. Upon further investigation, it was determined that this is likely due to the viscosity of the solutions at each concentration as follows

| Concentration of aztreonam | Viscosity of aztreonam |
|---|---|
| 75 mg/mL | 1.48 ± 0.1 mPas |
| 90 mg/mL | 1.7 ± 0.03 mPas |

These findings are counterintuitive and surprisingly show that the lower concentration of the drug, namely 75 mg/mL formulation is the best dose for the most efficacious delivery of aztreonam lysinate by inhalation.

5. Dry Powder, Aerosol and Aerbsol Suspensions

The formulation according to the invention contains aztreonam lysinate formulated as a dry powder, aerosol solution or aerosol suspension of liposomes or other microscopic particles in an aqueous solvent. The formulation is designed to be well tolerated and able to be reliably and completely nebulized to aerosol particles within the respirable size range of 1 to 5μ.

The doses are designed to contain as much as, but not more than, the necessary amount of a most active form of aztreonam lysinate to prevent colonization and/or to treat severe pulmonary infections caused by a range of susceptible gram-negative organisms.

Patients can be sensitive to pH, osmolality, and ionic content of a nebulized solution. Therefore these parameters are adjusted to be compatible with aztreonam lysinate chemistry and still tolerable to patients.

The formulation of the invention is nebulized predominantly into particle sizes allowing a delivery of the drug into the terminal and respiratory bronchioles where the bacteria reside during infection and in the larger airways during colonization.

For efficacious delivery of aztreonam lysinate to the lung endobronchial space of airways in an aerosol particle, the formation of an aerosol having a mass medium average diameter predominantly between 1 to 5μ is necessary. The formulated and delivered amount of aztreonam lysinate for treatment and prophylaxis of endobronchial bacterial infections must effectively target the lung surface. The formulation must have a smallest possible aerosolizable volume able to deliver an effective dose of aztreonam lysinate to the site of the infection. The formulation must additionally provide conditions which would not adversely affect the functionality of the airways. Consequently, the formulation must contain enough of the drug formulated under the conditions which allow its efficacious delivery while avoiding undesirable reactions. The new formulation according to the invention meets all these requirements.

One way to deliver inhalable aztreonam lysinate is by way of dry inhalable powder.

The aztreonam lysinate of the invention may be endobronchially administered in a dry powder formulation for efficacious delivery of the finely milled aztreonam powder into the endobronchial space using dry powder or metered dose inhalers as an alternative to aerosol delivery.

A dry powder formulation has potency, on a mass basis, which allows such alternative delivery of aztreonam lysinate as a dry powder using dry powder inhaler. A sufficiently potent formulation of aztreonam lysinate provides a dry powder which can be advantageously delivered by dry powder inhaler or by metered dose inhaler. For delivery of dry inhalable powder, aztreonam lysinate is milled, precipitated, spray dried or otherwise processed to particle sizes between about 1 and 5μ.

Dry powder formulation comprises from about 20 to 200 mg, preferably 10 to 100 mg of aztreonam lysinate.

For dry powder formulation of the invention, aztreonam lysinate is milled to a powder having mass median average diameters ranging from 1–5 microns by media milling, jet milling, spray drying or particle precipitation techniques as described in Example 6.

Briefly, for spray drying, aztreonam alpha form is suspended in water, stirred and cooled. L-Lysine dissolved in water is added slowly over about 3 to about 10 minutes, preferably about 6 minutes, until both components are almost completely dissolved. Solution is purified using a charcoal and filtered. Subsequently, the solution is spray dried using any suitable spay-drying equipment, such as, for example Buchi Mini Spray Dryer B-191.

Particle size determinations are made using a multi-stage Anderson cascade impactor or other suitable method. The Thermo Andersen Eight Stage Non-Viable Cascade Impactor is specifically cited within the US Pharmacopoeia Chapter 601 as a characterizing device for aerosols within metered-dose and dry powder inhalers. The Eight Stage Cascade Impactor utilizes eight jet stages enabling classification of aerosols from 9.0 micrometers to 0.4 micrometers (at 28.3 L/min) and allows airborne particulate to impact upon stainless steel impaction surfaces or a variety of filtration media substrates. A final filter collects all particles smaller than 0.4.

Media milling is accomplished by placing a drug substance into a mill containing, for example, stainless steel or ceramic balls and rotating or tumbling the material until the desired drug particle size ranges are achieved. Advantages of media milling include good size control, narrow product size ranges, high efficiencies of recovery, and readily scalable processes. Disadvantages include long manufacturing process times which takes from several hours to several days, the requirement that the milling media be separated from the product at completion, and the possibility of contamination of the product with the media.

Jet milling uses very high pressure air streams to collide particles with one another, with fine particles of the desired size being recovered from the mill. Advantages include rapidity of the manufacturing process and less energy transfer during milling, resulting in less temperature rise during the drug production. The jet milling process is completed in seconds to minutes. Disadvantages of the jet milling include poorer yield and collection efficiencies, with only 50 to 80% of recovery being a typical yield.

Spray-drying is another technique useful for preparation of inhalable dry powder. Spray drying involves spraying a fine mist of aztreonam lysinate solution onto a support and drying the particles. The particles are then collected. Spray drying has the advantage of being the least prone to degrading chemical entities. Adding a co-solvent which decreases the solubility of a drug to a uniform drug solution results in solution precipitation. When sufficient co-solvent is added, the solubility of the drug falls to the point where solid drug particles are formed which can be collected by filtration or centrifugation. Precipitation has the advantage of being highly reproducible, having a high yield of recovery and being able to be performed under low temperature conditions, which reduce degradation.

Dry powder inhalation and metered dose inhalations are more practical when administered doses result in the delivery of at least about 10 mg, and more preferably about 25 to about 100 mg, of aztreonam lysinate to the lung of the patient receiving treatment. Depending on the efficiency of the dry powder delivery device, which is typically about 70%, typical effective dry powder dosage levels fall in the range of about 20 to about 60 mg of aztreonam lysinate. Therefore, typically more than one breath of drug is required.

In this aspect, the invention provides a sufficiently potent formulation of pure aztreonam lysinate in dry powder or metered dose form of drug particles milled or otherwise prepared to particle sizes predominantly with a range of 1 to 5 microns. Such formulation is practical and convenient because it does not require any further handling such as diluting the dry powder or filling an aerosol container. Further, it utilizes the devices that are sufficiently small, fully portable and do not require, for example, an air compressor which is needed for a jet nebulizer. Additionally, the dry powder formulation has a longer shelf life that the liquid aztreonam lysinate formulations for aerosolization. Aztreonam lysinate, when reconstituted into an aerosolizable solution, has only a limited shelf life at room temperature due to hydrolysis of the monobactam ring. Aztreonam lysinate dry powder does not have this problem.

The dry powder formulation is thus practical and convenient for ambulatory use because it does not require dilution or other handling, it has an extended shelf-life and storage stability and the dry powder inhalation delivery devices are portable and do not require an air compressor needed by aerosol nebulizers.

All techniques suitable for preparation of dry inhalable powders and any and all improvements thereof as well as any dry powder inhaler are intended to be within the scope of the invention.

B. Stability, Shelf-Life and Storage

Stability of the formulation is another very important issue for efficacious formulation. If the drug is degraded before aerosolization, a smaller amount of the drug is delivered to the lung thus impairing the treatment efficacy. Moreover, degradation of stored aztreonam lysinate may generate materials that are poorly tolerated by patients.

The dry form of aztreonam lysinate has at least 2 years long shelf life. The liquid forms of the aztreonam/arginine have a 24-hour stability at room temperature, 48 hours when refrigerated, and when frozen at −4° C., such stability can be extended to about three months. However, the stability of aztreonam arginine salt is an attribute of arginine. The stability of other salts, after liquid reconstitution may differ.

A long-term stability of aztreonam free base or aztreonam lysinate in aqueous solution may not provide a sufficiently long shelf life-which would be commercially acceptable. A liquid formulation, therefore, may require a separation of aztreonam lysinate from the appropriate diluent. For this reason, the formulation is preferably supplied in a dry form and can be a reconstituted prior to administration as described below.

A formulation for aerosolization is thus preferably provided as two separate components, one containing a dry aztreonam lysinate containing an appropriate diluent such as 0.1 to 0.9 N saline, bicarbonate or any equivalent aqueous solution, as described above. The formulation is reconstituted immediately prior to administration. This arrangement prevents problems connected with the long-term stability of aztreonam lysinate in aqueous solvents.

According to the invention, aztreonam lysinate for aerosolization is preferably formulated in a lyophilized dosage form intended for use as a dry powder for reconstitution before inhalation therapy. The formulation of aztreonam lysinate can be aseptically prepared as a lyophilized powder either for dry powder delivery or for reconstitution and delivery, or as a frozen solution, a liposomal suspension, or as microscopic particles. The storage suitability of the formulation allows reliable reconstitution of the formulated aztreonam lysinate suitable for aerosolization.

C. Formulation for Inhalation-Packaging

The formulation of the invention is packaged for delivery to a patient in a package comprising several components.

Exemplary formulation package, consists of two separately packaged components: the lyophilized aztreonam-lysine powder and the sterile saline diluent to reconstitute the powder prior to delivery by nebulization.

Each vial contains 90–110% of labeled amount of Aztreonam (75 mg) and Lysine (47 mg) as aztreonam lysinate. Aztreonam and lysine form an ionic salt, which readily dissolves in saline. The diluent is a sterile 1 mL vial of 0.17% Sodium Chloride Inhalation Solution (0.17 mg/mL NaCl). After reconstitution with 0.17% NaCl, the pH of the solution is 4.2–7.0 and the osmolality is from 350 to 500 mOsmol/kg. The aztreonam related impurities are the following: open-chain aztreonam, desulfonated aztreonam, aztreonam E-isomer, and t-Butyl-Aztreonam. The total impurities are less than 1%. Each known contaminant is less than <0.2%. Unknown impurities are less than <0.1%. All ingredients meet USP requirements with the exception of lysine monohydrate, which currently has no monograph in the USP. The formulation contains no preservatives.

III. Administration of Aztreonam Lysinate by Inhalation

Aztreonam lysinate is currently not available. The only available form of aztreonam is aztreonam arginine for parenteral use. Arginine is known to cause pulmonary inflammation and irritation, as discussed above, and is, therefore, unsuitable for inhalation use.

A. Two Modes of Inhalable Administration

Administration of inhalable aztreonam lysinate is achieved either with aztreonam lysinate aerosol or with inhalable dry aztreonam lysinate powder.

An arginine free formulation according to the invention delivered by inhalation has been shown to safely treat respiratory infections caused by all susceptible gram-negative bacteria including *Pseudomonas aeruginosa, Escherichia coli, Klebsiella pneumoniae, Pseudomonas aeruginosa, Haemophilus influenzae, Proteus mirabilis, Enterobacter* species and *serratia marcescens,* as well as, and more importantly, antibiotics resistant strains *Burkholderia cepacia, Stenotrophomonas maltophilia, Alcaligenes xylosoxidans,* and multidrug resistant *Pseudomonas aeruginosa.*

B. Frequency of Dosing

Treatment of pulmonary infections caused by the above named bacteria is achieved by a treatment regimen which provides one to several, preferably one to two, times a day an inhalable aztreonam lysinate. Most preferred dosing regimen for patient covenience is once or twice a day, however, because of a specific effect aztreonam lysinate asserts on the bacteria, and because of its relatively short life-time of about 12 hours, more often dosing is sometimes required for complete eradication of the bacteria from the endobronchial space.

In patients with severely impaired lung function, the frequency of dosing may be increased up to about twelve times a day each time, providing only such amount of aztreonam lysinate as necessary to maintain therapeutic level in the lung.

Aztreonam lysinate kills bacteria by lysing cell walls as long as the local concentration of antibiotic exceeds the bacteria minimal inhibitory concentration (*Med. Clinics N, Am.*, 79: 4, 733–743 (1995)). Because of the relatively rapid clearance of antibiotics from the respiratory tract due to mucociliary action, greater efficacy is obtained at a lower dose of administered aztreonam lysinate by treating a patient three, four or more times a day rather than administer the drug only once or twice. To this effect the aztreonam lysinate dose delivered by inhalation is at least four times and can be one thousand time lower then the aztreonam arginine dose delivered intravenously or utilized in the one attempt described above to deliver aztreonam arginine by aerosolization where 500–1000 mg was delivered twice a day to a total amount of 1000 mg for children under 5 years of age and 2000 mg for individuals older than 5 years.

The current daily doses of aztreonam lysinate can be as small as 2 mg. The typical upper limit is 500 mg of aztreonam lysinate per day delivered in two to four administrations. In extreme cases the dose may reach up to 750 mg per day delivered in three, four or more aerosol administrations. Typical and preferred range for one aerosol dosage is between 20 and 200 mg administered twice a day or between 10 and 100 mg administered three or four times per day. Most preferred dose is 75 mg/ml delivered twice or more times a day.

Aerosolization of aztreonam lysinate utilizes delivery of aerosolized aztreonam lysinate using atomizing, jet, ultrasonic, electronic or other equivalent nebulizers. Portable nebulizers, such as atomizing, ultrasonic and electronic nebulizers are preferred for ambulatory treatment. The jet nebulizers with a compressor nebulize the aztreonam lysinate formulation very efficiently but are more suitable for use in the hospital and doctor's office.

A dry powder inhalation, as the second mode of administration of the inhalable aztreonam lysinate utilizes the aztreonam lysinate dry powder formulation. Such formulation comprises a delivery of the finely milled aztreonam lysinate directly to the endobronchial space. In this instance, aztreonam lysinate is delivered into the endobronchial space using dry powder or metered dose inhalers. The aztreonam lysinate potency, determined on a mass basis, allows the inhalation of aztreonam lysinate powder, as an alternative mode of administration to the aerosol. Dry powder inhalation is most efficacious, practical and economical when administered doses contain less than 100 mg. The frequency of dosing, thus, is typically three or four times a day but also includes one or two or more than four times dosing regimen as this regimen depends on the need and condition of the patient.

The invention provides a sufficiently potent formulation of aztreonam lysinate in a form of dry powder delivered as metered dose inhalation of aztreonam lysinate particles milled or spray dried to particle sizes predominantly within a range of 1 to 5μ. Such dry powder delivery is possible and preferable particularly for ambulatory inhalation as it simplifies the delivery process. Such delivery is convenient because it does not require any further handling such as diluting the dry powder or mixing the powder with a solvent, etc. Further, the dry powder inhalation utilizes the devices that are sufficiently small, fully portable and do not require, for example, an air compressor which is needed for a jet nebulizer. Additionally, the dry powder formulation has even longer shelf life than the liquid aztreonam lysinate formulation for aerosolization.

The dosing regimen for both aerosol and dry powder aztreonam lysinate comprises from one to four, typically, or more than four times daily, in untypical cases, administration of the aerosol or dry powder.

Severely impaired cystic fibrosis patients, for example, may be able to withstand only one inhalation at a time but could repeat this inhalation of small amount of aztreonam lysinate every two, three or four hours to obtain sufficient level of aztreonam lysinate in the lungs.

IV. Devices for Delivery of Aerosolized Aztreonam Lysinate

A primary requirement of this invention is to deliver aztreonam lysinate efficiently to the endobronchial space of airways in a most economic way. Thus, the invention requires that at least 30–50%, preferably 70–90% of the active drug, that is aztreonam lysinate subjected to nebulization is in fact delivered to a site where it asserts its therapeutic effect.

A. Nebulizers

The composition of the invention described above provides the drug formulated in a solution permitting delivery of a therapeutically efficient amount of the drug, provided that the aerosol generated by the nebulization meets criteria required for such efficient delivery. The apparatus (nebulizer) which aerosolizes the formulation of aztreonam lysinate thus becomes a very important part of the invention.

There are quite a few nebulizer types currently commercially available. Not all of them are suitable for practicing this invention.

A nebulizer is selected primarily on the basis of allowing the formation of aztreonam lysinate aerosol having a mass medium average diameter predominantly between 1 to 5μ. The delivered amount of aztreonam lysinate must be efficacious for treatment and prophylaxis of endobronchial infections, particularly those caused by susceptible bacteria. The selected nebulizer thus must be able to efficiently aerosolize the formulation which has salinity, osmotic strength, and pH adjusted as to permit generation of aztreonam lysinate aerosol that is therapeutically effective and well tolerated by patients. The negulizer must be able to handle the formulation having a smallest possible aerosolizable volume and still able to deliver effective dose of aztreonam lysinate to the site of the infection. Additionally, the aerosolized formulation must not impair the functionality of the airways and must minimize undesirable side effects.

The inability of certain nebulizers to nebulize therapeutic quantities of drugs into small and uniform particle size aerosols is well known. For efficacious delivery of aztreonam lysinate a range of aerosolized particles with MMAD needed to deliver the drug to the endobronchial space, the site of the infection, is between 1–5μ. Many commercially available nebulizers are able to aerosolize large volumes of the solution with an aim to deliver at least 10% of the volume to the endobronchial space by producing around 90% of large aerosol particles above 5μ with a very large number of particles being in the range of 50–100μ. These nebulizers are inefficient and not suitable for delivery of aztreonam lysinate according to this invention.

In order to be therapeutically effective, the majority of aerosolized aztreonam lysinate particles should not have larger mass medium average diameter (MMAD) than between 1 and 5μ. When the aerosol contains a large number of particles with a MMAD larger than 5μ, these are deposited in the upper airways decreasing the amount of antibiotic delivered to the site of infection in the lower respiratory tract.

Previously, two types of nebulizers, jet and ultrasonic, have been shown to be able to produce and deliver aerosol particles having sizes between 1 and 5µ. These particle size are optimal for treatment of pulmonary bacterial infection cause by gram-negative bacteria such as *Pseudomonas aeruginosa, Escherichia coli, Enterobacter* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans,* and multidrug resistant *Pseudomonas aeruginosa*. However, unless a specially formulated solution is used, these nebulizers typically need larger volumes to administer sufficient amount of drug to obtain a therapeutic effect. Therefore, without a specially formulated aztreonam lysinate the efficient delivery of aztreonam lysinate is not achieved.

Nebulizer suitable for practicing this invention must be able to nebulize a small volume of the formulation efficiently, that is into the aerosol particle size predominantly in the range from 1–5µ. Predominantly in this application means that at least 70% but preferably more than 90% of all generated aerosol particles are within 1–5µ range.

Jet and ultrasonic nebulizers can produce and deliver particles between the 1 and 5µ particle size. A jet nebulizer utilizes air pressure breakage of an aqueous aztreonam lysinate solution into aerosol droplets. An ultrasonic nebulizer utilizes shearing of the aqueous aztreonam lysinate solution by a piezoelectric crystal.

Typically, however, the jet nebulizers are only about 10% efficient under clinical conditions, while the ultrasonic nebulizer are only about 5% efficient. The amount deposited and absorbed in the lungs is thus a fraction of the 10% in spite of the large amounts of the drug placed in the nebulizer.

One type of nebulizer which is suitable and preferred for aztreonam lysinate delivery is an atomizing nebulizer which consists of a liquid storage container in fluid contact with the diaphragm and inhalation and exhalation valves. For administration of the aztreonam lysinate formulation, 1 to 5 ml of the formulation is placed in the storage container, aerosol generator is engaged which produces atomized aerosol of particle sizes selectively between 1 and 5µ.

Typical nebulizing devices suitable for practicing this invention include atomizing nebulizers, or modified jet nebulizers, ultrasonic nebulizers, electronic nebulizers, vibrating porous plate nebulizers, and energized dry powder inhalers modified for handling small volume of highly concentrated drug in a specific formulation having a specific pH, osmolality and salinity. Most preferred nebulizer is the PARI inhalation nebulizer described in PCT/US00/29541 modified to meet the requirements of this invention.

B. Dry Powder Inhalers

Dry powder is administered as such using devices which deliver the dry powder directly to the lungs.

There are two major designs of dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of drug into small particles of mass median diameters from 1 to 5 microns, and usually involve co-formulation with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

Current technology for dry powder inhalers is such that payload limits are around 100 mg of powder. The lack of long-term stability of aztreonam lysinate in an aqueous solution due to hydrolysis allows dry powder inhaler technology to become a preferred delivery vehicle for aztreonam lysinate dry powder.

C. Aerosol or Dry Powder Particle Size

Particle size of the aztreonam lysinate aerosol formulation is one of the most important aspect of the invention. If the particle size is larger than 5µ then the particles are deposited in upper airways. If the particle size of the aerosol is smaller the 1µ then it does not get deposited in the endobronchial space but continues to be delivered into the alveoli and may get transferred into the systemic blood circulation.

A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes. However, only some formulations of aztreonam lysinate can be efficiently nebulized as the devices are sensitive to pH and salinity.

In dry powder inhalers, the aztreonam lysinate dry powder prepared as described above in dosages from 1–100 mg, preferably from 10–50 mg of dry powder as particles having sizes between 1 and 5µ, is used directly.

D. Efficacy of Aztreonam Lysinate Nebulization

Selection and choice of the nebulizer greatly effects efficacy of the inhalable aztreonam lysinate delivery.

A combination of an aerosol formulation of aztreonam lysinate and a nebulizing device significantly enhance the efficiency and speed of drug administration. Currently, for example the average time for administration of other aerosolized drugs, such as for example tobramycin, is 15–20 minutes per dose. The time required for this treatment represents a significant burden to the patient and contribute to reduced compliance with the BID regimen.

Furthermore, the nebulizer system used for tobramycin administration is less efficient than new atomizing devices. The total deposited dose of tobramycin in the lung is in the 12 to 15% range. Approximately 30% of the dispensed drug remains in the nebulizer at the end of treatment, and of the portion that is aerosolized, about 30% is emitted as particles too large or small to reach the lower airways.

The novel atomizing nebulizer, with an output of 8 to 10 microliters/seconds, or 0.48 to 0.60 ml/minute, is capable of delivering drug material 2 to 4 times faster than the prior nebulizers exemplarized by PARI LC plus nebulizer. Furthermore, the novel nebulizer is able to aerosolize approximately 90% of the dispensed dose, with 85% or more of the aerosol particles being within the size range required for lower airway deposition. As a result, administration of a specifically designed formulation of aztreonam lysinate using the atomizing nebulizer leads to substantial improvement in local delivery to the airways, to a shorter time required for delivery and, depending on the final concentration of aztreonam lysinate solution, reduces treatment time to as little as three or four minutes.

V. Supporting Experimental Studies

*Pseudomonas aeruginosa* is the most common cause of chronic endobronchial infection in cystic fibrosis (CF) patients. This infection is a major cause of morbidity and mortality in these patients. Topical application of antibiotic agents inhaled as aerosol mists has demonstrated significant benefit to CF patients. Aerosolized antibiotic therapy with agents including carbenicillin, gentamicin, ticarcillin, tobramycin, and colistin but not aztreonam has been practiced for many years.

The most widely used aerosolized antibiotic for treatment of CF patients is tobramycin, which produces substantial improvements in pulmonary function and other clinical parameters. In vitro, tobramycin is active against most *P. aeruginosa* organisms in the absence of sputum; however, in the presence of sputum, tobramycin bioactivity is significantly reduced.

Aztreonam is a monobactam antibiotic with excellent activity against many aerobic gram-negative bacteria, including *P. aeruginosa*. It is currently approved as parenteral therapy for a variety of serious infections and has been widely used in control of pulmonary exacerbations in CF patients. Aztreonam has an antibacterial spectrum similar to the aminoglycoside antibiotics tobramycin and gentamicin. Its excellent activity against many aerobic gram-negative bacteria, including *P. aeruginosa*, has led to widespread use among CF patients, including intravenous administration as single agent therapy and in combination with other antibiotics for treatment of pulmonary exacerbations. These studies have demonstrated improvement in pulmonary function and clinical scores, as well as reductions in bacterial load and white blood cell counts. Additionally, aztreonam have been shown to have a potential for control of *Burkholderia cepacia*, a pathogen intrinsically resistant to the commonly used aminoglycoside antibiotics.

In order to determine whether aztreonam would be successful for treatment of *P. aeruginosa* and other bacterial infections, in the presence of sputum or mucin antagonized aztreonam bioactivity in vitro was investigated.

Experimental conditions are described in Example 8.

Results of these studies are described in FIGS. 1 to 3 which represent antibiotic killing curves obtained with different concentrations of the antibiotics aztreonam (FIGS. 1 and 2) and tobramycin (FIG. 3), in the presence or absence of mucin or CF sputum. Mucin is a model for the protein binding component of sputum.

FIG. 1 illustrates aztreonam activity against *P. aeruginosa* in the absence (FIG. 1A) or presence (FIG. 1B) of hog gastric mucin. Aztreonam was added to yield a final concentration in the following multiples of the MIC: 0.0 (♦); 0.1 (□); 1.0 (■); and 10 (◇).

As seen in FIG. 1, the curves without hog gastric mucin (FIG. 1A) and without hog gastric mucin (FIG. 1B) are virtually identical, indicating no measurable inhibition of the antibiotic by mucin.

FIG. 2 shows aztreonam activity against *P. aeruginosa* in the presence or absence of cystic fibrosis (CF) sputum. Aztreonam was added to yield a final concentration in the following multiples of the MIC: 0.0 (♦); 0.1 (□); 1.0 (■); and 10 (◇).

As seen in FIG. 2, the curves without CF sputum (FIG. 2A) and without sputum (FIG. 2B) are virtually identical, indicating no measurable inhibition of the antibiotic by CF sputum.

Tobramycin, which is known to bind mucins and to be inhibited by sputum and mucin, was tested with or without mucin in the same assay for comparative purposes.

Figures 3A, 3B:
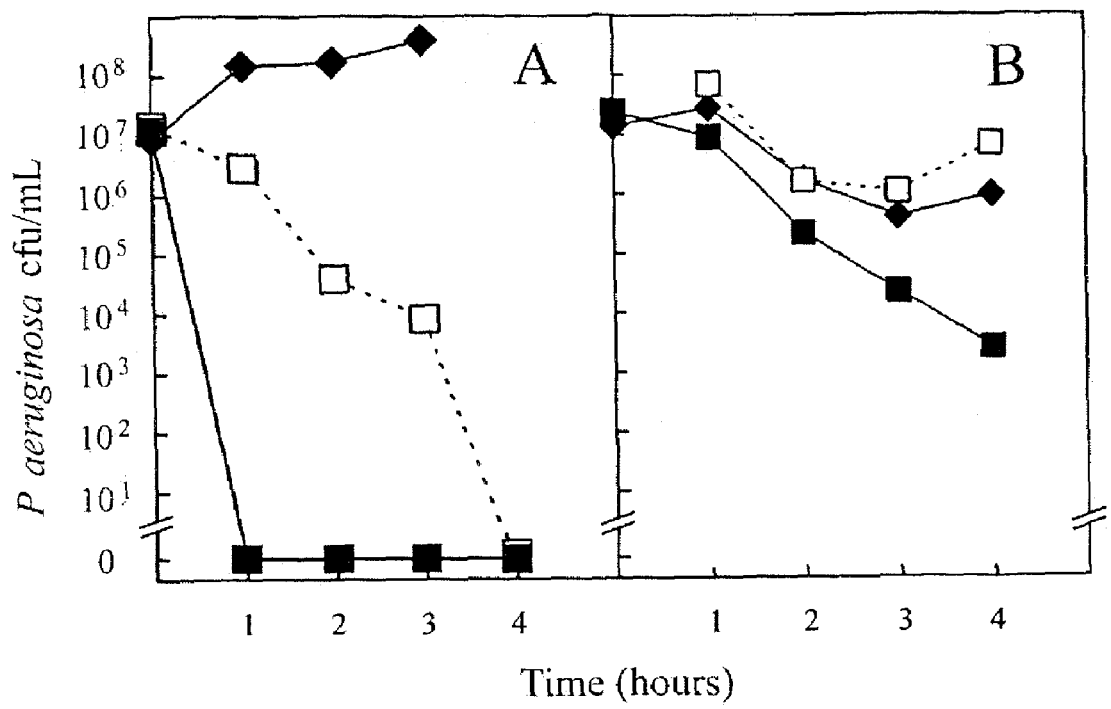

FIG. 3 shows tobramycin activity against *P. aeruginosa* in the absence (FIG. 3A) or presence (FIG. 3B) of added mucin. Tobramycin was added to yield a final concentration in the following multiples of the MIC: 0.0 (♦); 1.0% (□); and 10% (■).

FIG. 3 demonstrates the ability of hog mucin to inhibit the activity of tobramycin. In the absence of mucin, tobramycin killed *P. aeruginosa* effectively, reducing colony counts by seven logs in one hour when applied at 10×MIC. In contrast, the same concentration of tobramycin in the presence of mucin caused much less killing: negligible amounts at one hour and only three to four logs at four hours. At 1×MIC, tobramycin killed seven logs of *P. aeruginosa* in four hours in the absence of mucin, but killed less than one log at four hours in the presence of mucin.

Neither CF sputum nor hog gastric mucin showed significant inhibition of the activity of aztreonam under the conditions of this assay. The *P. aeruginosa* killing curves obtained were virtually identical to controls lacking sputum or mucin. Growth of *P. aeruginosa* occurred, as expected, when aztreonam was added in quantities less than the MIC (upper curves in all figures), while effective killing occurred when aztreonam was present at or above the MIC (lower curves).

This contrasts with the result for tobramycin, an antibiotic known to be inhibited by CF sputum and hog gastric mucin. Addition of mucin to tobramycin resulted in decreased killing by up to four logs, depending on timing and the concentration of antibiotic used. These results confirm the validity of the mucin inhibition assay as a model for interpreting expected outcomes in the lungs of CF patients.

These results show that aztreonam is not inhibited by sputum of cystic fibrosis patients and that it will not be inhibited as a primary or a secondary complementary treatment when administered by inhalation, at least not to the extent that tobramycin is. This implies that aztreonam may be preferable to tobramycin in the treatment of respiratory infections in cystic fibrosis or other patients, as more antibiotic will be available to eradicate *Pseudomonas aeruginosa*.

VI. Treatment of Pulmonary Bacterial Infections

This invention provides an efficacious treatment and prevention of acute and chronic pulmonary bacterial infections caused by *Pseudomonas aeruginosa, Escherichia coli, Klebsiella pneumoniae, Pseudomonas aeruginosa, Haemophilus influenzae, Proteus mirabilis, Enterobacter* species and *Serratia marcescens,* as well as infection caused by antibiotic resistant strains *Burkholderia cepacia, Stenotrophomonas maltophilia, Alcaligenes xylosoxidans,* and multidrug resistant *Pseudomonas aeruginosa.*

A. Two Modes of Inhalable Treatment

A method for treatment of pulmonary infections comprises administration of aztreonam lysinate in inhalable form whether by aerosol or as a dry powder, several times a day. The aztreonam lysinate daily dose is between 1 and 500 mg/day, with exceptional dose up to 750 mg/day administered in from 1–50 mg/ml for aerosol and from 2 to 200 mg daily dose of dry powder administered in a dose of 1–100 mg/one treatment. The aztreonam lysinate dosage and dosing frequency depends on the type of bacterial infection, severity thereof, age of the patient, the conditions of the patient, etc. In case of cystic fibrosis patients where the lung air capacity is diminished, the dosing is more frequent with lower doses.

The dry powder formulation suitable for treatment of pulmonary infections comprises 1 to 200 mg, preferably about 10 to 100 mg, of powder in an amorphous or crystalline state in particle sizes between 1 and 5 microns in mass median average diameter necessary for efficacious delivery of aztreonam lysinate into the endobronchial space. The dry powder formulation is delivered one to four or more times daily, preferably twice daily. The dry powder formulation is temperature stable and has a physiologically acceptable pH of 4.2–7.5, preferably 5.5 to 7.0, and an over five year long shelf life.

B. Treatment of Infections in Patients with Suppurative Pulmonary Diseases

Aerosol therapy of this invention is particularly useful for treatment of patients suffering from suppurative pulmonary diseases and is especially suitable for treatment of patients with cystic fibrosis, bronchiectasis and those patients on the mechanical ventilation.

Previously, aerosol therapy for cystic fibrosis inhaled (ATCF) antibiotics have demonstrated significant benefit of such treatment to cystic fibrosis (CF) patients suffering from chronic pulmonary infections.

In the US, the most widely used and successful agent in this regard has been tobramycin, which has been shown to produce substantial improvements in lung function and other clinical parameters.

It has now been discovered that inhalable aztreonam lysinate provides successful treatment in cystic fibrosis, bronchiectasis or other suppurative pulmonary disease for pulmonary infections caused by gram-negative bacteria and particularly those caused by antibiotic resistant *Burkholderia cepacia, Stenotrophomonas maltophilia, Alcaligenes xylosoxidans* and multidrug resistant *Pseudomonas aeruginosa*.

Treatment of these multi-resistant bacterial infections with aerosolized aztreonam lysinate has been successful in eradication of the bacteria as described in Example 2.

Such treatment is either stand alone or may be complementary treatment to other antibiotics, such as tobramycin, which upon extended use, results in the development of anti-tobramycin resistance. When the treatment with tobramycin is interspaced with periods of treatment with aztreonam lysinate, such resistance either does not develop or recedes.

C. Limitations of Current Aerosolized Antibiotics in Treatment of Cystic Fibrosis To date, an aminoglycoside tobramycin is the only antibiotic with FDA approval for administration as an aerosol. However, despite the benefits obtained in cystic fibrosis patients with administration of aerosolized tobramycin, its utility is somewhat limited.

First, frequent use of aminoglycosides to control pulmonary exacerbations leads to selective development of resistant *Pseudomonas aeruginosa* strains. The widespread emergence of such organisms is acknowledged as a growing crisis in the CF community. For example, 21% of patients screened from 69 different CF centers for the phase III tobramycin clinical trials had isolates resistant to tobramycin (MIC >16 µg/mL). Accordingly, many clinicians are reluctant to prescribe this aerosolized aminoglycoside as chronic suppressive therapy, fearing that it could further promote resistance and thus diminish the effectiveness of IV therapy. In order to reduce the risk of such treatment-emergent resistance, tobramycin therapy is restricted to cycles of 28 days on and 28 days off the drug.

A second limitation of aerosolized tobramycin is its lack of activity against several intrinsically tobramycin resistant bacteria, including *Stenotrophomonas maltophilia, Alcaligenes xylosoxidans,* and *Burkholderia cepacia,* the latter of which is widely recognized as a significant threat to cystic fibrosis patients. Cystic fibrosis patients infected with *Burkholderia cepacia* have an increased rate of mortality, and many experience a rapid fatal course, as described in *Am. J. Respir. Crit. Care Med.,* 160:1572–1577, (1999). Additionally, *Burkholderia cepacia* is a transmittable infection which can cause epidemic spread among cystic fibrosis patients. Therefore, a patient infected with *Burkholderia cepacia* must be isolated from other patients.

Aerosolized aztreonam lysinate does not induce resistance to aminoglycosides and has good activity against resistant pathogens observed in cystic fibrosis patients.

An aerosolized aztreonam lysinate can either replace tobramycin, or be used as an alternative and intermittent treatment for tobramycin during the 28-day tobramycin free periods, which are required to prevent development of permanent resistence to tobramycin.

Aztreonam lysinate is an antibiotic with excellent activity against many aerobic gram-negative bacteria, including multi-resistant *Pseudomonas aeruginosa*. The spectrum of activity of aztreonam lysinate is similar to that of the aminoglycoside antibiotics tobramycin and gentamycin, and its antipseudomonal activity is comparable to ceftazidine and in several aspects, it is better than tobramycin. For example, aztreonam lysinate is not inhibited by CF patient sputum, making it much more potent drug than tobramycin which is so inhibited.

Aztreonam lysinate resists destruction by most bacterial β-lactamases, which are the source of much treatment-emergent resistance to β-lactam antibiotics frequently appearing among hospitalized patients.

Aztreonam lysinate's activity against gram-negative bacteria, especially *Pseudomonas aeruginosa,* combined with its excellent safety profile makes it a good alternative to aminoglycosides in the treatment of chronic pulmonary infections among cystic fibrosis patients. Thus far, clinical use of aztreonam lysinate in CF patients has included IV administration of aztreonam as single agent therapy or in combination with other antibiotics for treatment of pulmonary exacerbations.

D. Advantages of Aztreonam Lysinate as an Aerosolized Antibiotic

Aztreonam lysinate possesses several features that make it very attractive for aerosol administration to CF patients.

The first of these features stems from its mechanism of action, which, unlike aminoglycoside antibiotics, involves preferential binding to penicillin binding protein 3 (PBP3) and subsequent interference with bacterial cell wall synthesis. Because aztreonam lysinate's mechanism of action differs from that of tobramycin, its use does not contribute to emergence of aminoglycoside-resistant strains of *Pseudomonas aeruginosa.*

The second advantage of an aerosolized formulation of aztreonam lysinate is its activity against tobramycin resistant, and multidrug resistant *Pseudomonas aeruginosa*. When isolates from patients enrolled in the Phase II tobramycin trials were examined, nearly 75% of isolates with a tobramycin MIC >16 µg/mL were susceptible to aztreonam lysinate.

The third feature is aerosolized aztreonam lysinate ability to control intrinsically tobramycin resistant organisms, especially *Burkholderia cepacia,* which is considered resistant to the levels of aztreonam lysinate achieved by parenteral administration.

VII. Antibacterial Activity of Aztreonam

In order to test antibacterial activity of aerosolized aztreonam against multi-resistant strains of *Pseudomonas aeruginosa, Burkholderia cepacia, Stenotrophomonas maltophilia* and *Alcaligenes xylosoxidans*, the in vitro activities of aztreonam in concentrations corresponding to those achievable with inhalable aztreonam were tested against clinical isolates from cystic fibrosis patients.

The aztreonam aerosol delivery according to the invention achieves concentrations of aztreonam to reach levels from 500 to as high as 8000 µg/ml, with an average level around 2,000 µg/ml, of aztreonam in the sputum. These levels depend on the formulation as well as on the nebulizer used for aerosolization. With certain nebulizers the concentration of aztreonam can reach an average level of 5,000 µg/ml.

In vitro determined susceptibilities of the tested bacteria is predictive of clinical efficacy of inhaled aztreonam aerosol or dry powder.

Aztreonam kills by lysing cell walls as long as the local concentration of antibiotic exceeds the bacteria minimal inhibitory concentration (*Med. Clinics N. Am.*, 79: 4, 733–743, (1995)).

The in vitro activity of high aztreonam concentrations against clinical isolates of *B. cepacia, S. maltophilia* and *A. xylosoxidans* was tested at the Children's Hospital and Regional Medical Center in Seattle, Wash. Testing was performed on broth microdilution trays made with 2 fold concentrations of aztreonam from 2 to 2048 µg/mL. *Staphylococcus aureus*, a gram positive organism, was used as a negative control.

Detailed procedure used for testing is described in Example 1. Results are seen in Table 1.

TABLE 1

| Organism (# of isolates) | MIC Range | MIC50 | MIC90 |
| --- | --- | --- | --- |
| P. aeruginosa (54) | 2–1024 | 16 | 512 |
| B. cepacia (38) | 2–2048 | 32 | 512 |
| S. mallophilia (20) | 8–>2048 | 256 | >2048 |
| A. xylosoxidans (20) | 2 > 2048 | 256 | 2048 |
| S. aureus (20) | 512–2048 | 1024 | 2048 |

For testing, each microwell plate contained a 2-fold dilution, 2, 4, 8, 16, 32, 64, 128, 256, 512, 1024 and 2048 of aztreonam. Each plate containing the microwells was used to test one isolate of one organism.

Table shows the different species of bacteria tested for sensitivity, that is the ability of the antibiotic to inhibit its growth, to aztreonam, with the number of isolates for each species given in parenthesis. The column designated "MIC range" shows the range of the lower and upper limits of sensitivities seen in the tested isolates. The column designated MIC50 shows the median level of sensitivity for the most sensitive 50% isolates. The final column, designated MIC90, shows the median value for the level of sensitivity for the most sensitive 90% of the isolates.

Table 1 shows results of comparative in vitro activity of aztreonam against clinical isolates obtained from cystic fibrosis patients.

For interpretation of this data, the values which represent what concentration of aztreonam is required to inhibit growth of bacteria are compared with the concentrations of aztreonam obtainable by the different routes of administration. Thus, for intravenous administration of aztreonam, the serum level following administration of 2 g of aztreonam, the maximum allowed intravenous dose, the serum level peak is 256 µg/ml and then declines rapidly. At six hours following the administration, the aztreonam level in the serum is in the range of 16 µg/ml. For safety reasons, intravenous aztreonam arginine can only be administered every six hours. With the possible exception of *Pseudomonas aeruginosa* that has a MIC50 of 16 µg/ml, all other organisms would be predominantly resistant to intravenous aztreonam, as their level of resistance exceeds even the peak concentration (256 µg/ml) of serum concentration of sputum of aztreonam following intravenous administration. Since, however, the bacteria resistance is relative to drug concentration, for aerosol administration, the peak concentration should be at least in the 500 to 2000 µg/ml range. Such range is achieved with the doses of aztreonam and the formulation of the invention combined with the efficient nebulizer, according to this invention. At the 500–2000 µg/ml concentration in the sputum, the aerosol therapy according to this invention is able to treat most endobronchial infections caused by gram-negative bacteria, specifically those bacteria listed in Table 1, with exception of *Staphyloccocus aureus*.

The MIC50 and MIC90 have shown that treatment of *P. aeruginosa* with inhalable aztreonam eradicates most *P. aeruginosa* isolates with the high concentrations of aztreonam in sputum of cystic fibrosis patients obtainable after aerosol delivery. The data obtained for *Burkholderia cepacia* isolate indicated that at least half of patients would be expected to respond to such treatment with eradication of the bacteria. If sufficiently high concentrations of aztreonam are delivered to the lung, the percentage is expected to be higher. Since the *Burkholderia cepacia* infection is now viewed as a largely untreatable condition, treatment with inhalable aztreonam by aerosol is the first documented efficacious therapy.

The results obtained in these studies are surprising and unexpected as there is no indication in the literature that *Burkholderia cepacia* is susceptible to treatment with aztreonam. The data also shows that some isolates of *S. maltophilia* and *A. xyloxidans* respond to high concentration of aztreonam.

Inhalation of aztreonam according to the invention permits reaching concentrations of aztreonam in the sputum as high as 2000–5,000 µ/mL. The sputum aztreonam levels achieved via aerosol administration exceed those required to inhibit organisms responsible for otherwise untreatable infections in CF patients.

Furthermore, aztreonam delivered by inhalation to all patients with *Burkholderia cepacia* and/or *S. maltophilia* and/or *A. xyloxidans* together with other antibiotics whether administered systemically parenterally or by inhalation contributes to synergy of such treatment. A combination of inhalable aztreonam with other antibiotics provides another therapeutic approach to treat multi-resistant bacterial strains.

The studies described herein demonstrated that the concentrations of aztreonam achieved following aerosol administration have activity against *Burkholderia cepacia* isolated from CF patients' sputum as well as against other bacteria which are largely resistant to treatment with other antibiotics.

The MIC50 and MIC90 observed for a gram positive bacteria, *Staphylococcus aureus*, show that high concentrations of aztreonam had some activity against this gram positive bacteria. These findings, however, have no great significance as there are many other drugs with reasonable efficacy against *Staphyloccocus aureus*.

VIII. Safety and Clinical Testing

The infections requiring particular attention are infections caused by and include *B. cepacia, S. maltophilia* and *A.*

*xylosoxidans*, as well as multi-resistant strains of *Pseudomonas aeruginosa*. The most clinical significant infection is the former.

In order to determine if an appropriately formulated aztreonam lysinate for aerosolization could become effective for treatment of these rare but very resistant bacterial strains, the treatment with aerosolized aztreonam lysinate was initiated and tested in a cystic fibrosis patient having a severe *Burkholderia cepacia* infection which did not respond to any treatment. The clinical treatment and results obtained with an aerosolized aztreonam lysinate is described in Example 2.

Safety of the aztreonam lysinate formulation was also studied both in man and in Beagle dog. Conditions of these studies are described in Samples 11 and 12.

Results of both studies confirm the safety of the aztreonam lysinate formulation for inhalation. As compared to a formulation containing arginine, the new formulation is safe in man (Example 10) and in dog at up to 200 fold of the human dose shown in a 28 day dog study (Example 11). Increased safety establishes utility of the aztreonam lysinate in both instances.

Safety results from both studies show that there were no serious adverse events recorded during the trial and no subject was withdrawn from the trial because of an adverse event. In total, 7 post-dose adverse events were reported for 7 subjects. No single adverse event was experienced by more than one subject. A single drug-related adverse event occurred in each of the 95 and 190 mg inhaled aztreonam dose groups (headache and dizziness, respectively) and 2 drug-related adverse events occurred in the 285 mg inhaled aztreonam dose group (dysgeusia, i.e. unpleasant taste and cough). One adverse event was of Grade 2 severity (headache) and the remaining adverse events were of Grade 1 severity. All adverse events resolved before the end of the trial. The adverse event of cough led to discontinuation of the trial medication, although the subject continued in the trial and completed all trial assessments.

There were no notable mean changes from baseline in any post-dose pulmonary function parameter. One subject, who was dosed with placebo, had an $FEV_1$ decrease from baseline of greater than 15% (+30 min). This was recorded as an adverse event, but was not considered to be related to the trial medication.

There were no notable mean changes from baseline in any hematology or coagulation parameter assessed.

There were no notable mean changes from baseline in systolic and diastolic pressure, pulse rate, oral temperature, respiration rate or pulse oximetry in subjects dosed with placebo or 90 mg, 190 mg or 285 mg inhaled aztreonam. No individual subject value in any of these parameters was reported as an adverse event.

There were no notable mean changes from baseline in any ECG parameter assessed and no individual subject ECG value was reported as an adverse event. No changes from baseline were noted on any post dose physical examination.

In conclusion, inhaled aztreonam was generally safe and well tolerated when administered at does of 95 mg, 190 mg and 285 mg in this trial.

There were no clinically significant changes in $FEV_1$ (defined as a decrease from baseline of 15% or more) in any subject treated with aztreonam. One subject who was treated with placebo experienced a decrease from baseline in $FEV_1$ of 15.58%. This was reported as an adverse event not considered to be related to treatment. There were no clinically significant changes in any other safety measurement (in either mean or individual values) there were considered to be treatment-related.

The objective of the second study was to assess the tolerability and toxicity of aerosolized aztreonam lysinate formulation in the Beagle dog after 28 day repeat dosing by the inhalation route and to evaluate the reversibility of any effects after a 14 day recovery period. Inhalation exposure was undertaken using a closed face-mask system with the dogs breathing passively from an ultrasonic nebulizer.

Conditions under which the study was conducted are described in Example 11.

Overall results of this study show that the inhalation of nebulized aztreonam lysinate is safe and there were no observed adverse clinical signs or treatment related effects on body weight, food consumption, ophthalmoscopic findings, ECG readings, laboratory investigations or organ weights.

There were no necropsy or histological findings that could be attributed to treatment with Aztreonam. Since the anticipated human dose is 75 mg, and the average weight is 75 kg, the safety margin may be as high as 200 fold over the human dose.

UTILITY

The method of treatment and the inhalable aztreonam lysinate compositions disclosed herein is suitable for treatment of respiratory tract infections caused by *Burkholderia cepacia, Stenotrophomonas maltophilia, Alcaligenes xylosoxidans,* and multidrug resistant *Pseudomonas aeruginosa* as well as for treatment of other pulmonary infections caused by gram-negative bacteria.

EXAMPLE 1

In vitro Testing of Isolates from Cystic Fibrosis Patients

This example describes procedure used for in vitro studies of bacterial isolates obtained from cystic fibrosis patients.

Bacterial respiratory tract isolates (144) from patients with CF that had been stored at −70° C. were cultivated by two consecutive overnight passages at 37° C. on 5% blood agar (Remel, Lenexa, Kans.).

Minimal inhibitory concentrations (MIC's) were determined by the following steps:

MIC Antimicrobial Testing Aerobic Organisms

1. MIC trays were brought to room temperature.
2. 3.0 ml physiological saline was inoculated with an 18–24 h culture of organism to be tested to a turbidity equal to a 0.5 McFarland Standard ($1.5 \times 10^8$ CFU/ml). This corresponds to an OD600 of 80–88% transmission.
3. Within 15 minutes of preparation, the adjusted inoculum suspension was diluted by transferring 100 ml into a 2.9 ml diluent of sterile water.
4. The suspension was gently mixed by inversion and 10 ml was dispensed into each MIC well having initial volume of 100 µl. The final concentration in each well was equal to $5 \times 10^5$ CFU/ml or $5 \times 10^4$ CFU/well.
5. Trays were incubated aerobically at 37° C. for 16–20 hours. The same incubation temperature was maintained for all cultures. Microdilution trays were not stacked more than four high.
6. Antimicrobial endpoint was read and recorded as the first well showing no readily visible growth or haze as detected by the unaided eye.

7. The microdilution trays were contacted with 2 fold concentrations of aztreonam lysinate from 2 to 2048 mg/mL. Each microwell plate was treated with a 2-fold dilution of aztreonam lysinate in following amounts: 2, 4, 8, 16, 32, 64, 128, 256, 512, 1024 and 2048 µg/ml. Each plate containing the microwells was used to test one isolate of one organism.

8. Results were read and recorded.

EXAMPLE 2

Clinical Treatment of Patient with *Burkholderia cepacia*

This example describes a first finding of efficacy of the aerosolized aztreonam treatment of a cystic fibrosis patient suffering from resistant *Burkholderia cepacia*.

The patient was a 20-year-old female with cystic fibrosis and end stage lung disease. She had been diagnosed with *Burkholderia cepacia* pulmonary infections that had become resistant to all known intravenous, oral and inhaled antibiotics. She had two-documented genetically different strains of *Burkholderia cepacia*. For this reason the patient was rejected as a candidate for a lung transplant.

The patient was provided with a formulation of the invention comprising 200 mg/ml of aztreonam and instructed to use this formulation in 3 to 5 ml of diluent and use it in an air compressor powered breath enhanced jet nebulizer and take the therapy twice a day. This type of nebulizer only delivers about 10 to 20% of the dose placed in the nebulizers to the lungs, however, that was only nebulizer available to the patient for home treatment.

After three months of continuous twice a day therapy, the pulmonary infection was successfully treated and no evidence of *Burkholderia cepacia* could be detected. The patient was considered treated from the infection and eventually underwent a successful lung transplant procedure.

There was no postoperative reoccurrence or relapse of the *Burkholderia cepacia* infection despite of intensive immunosuppression therapy following the transplantation.

These findings were surprising since previous use of commercially available aztreonam arginine in an older generation delivered in even less efficient nebulizers did not lead to eradication of *P. aeruginosa* as described in *Clinics Chest Med.*, 19:473–86, (September 1998). In the trial described there, the authors stopped therapy at the development of any aztreonam resistance rather than continuing treating these patients. Prior work did not test or speculate that this therapy could be effective in treating other gram negative bacteria including *Burkholderia cepacia, S. maltophilia, X. xylosoxidans*, or other multidrug resistant pseudomonas infections.

The results obtained with treatment of the above patient are even more surprising in that the eradication of *Burkholderia cepacia* is extremely rare occurrence, particularly when the infection is well established as was in the case of this patient.

EXAMPLE 3

Preparation of Aztreonam Lysinate Dry Powder

This example provide methods and procedures used for preparation of aztreonam lysinate containing inhalable dry powder.

For dry powder formulation of the invention, a purified aztreonam lysinate is milled to a powder having mass median average diameters ranging from 1 to 5µ by media milling, jet milling, spray drying, or particle precipitation techniques.

Particle size determinations is made using a multi-stage Anderson cascade impactor.

Media milling may be accomplished by placing the drug into a mill containing, for example, stainless steel or ceramic balls and rotating or tumbling the material until the desired drug particle size ranges are achieved.

Jet milling uses very high pressure air streams to collide particles with one another, with fine particles of the desired size being recovered from the mill.

Spray drying is achieved by spraying a fine mist of drug solution onto a support and drying the particles. The particles are then collected.

Particle precipitation is achieved by adding a co-solvent to spray dried particles. The solubility of the drug falls to the point where solid drug particles are formed. The particles are collected by filtration or centrifugation. Precipitation has the advantage of being highly reproducible and can be performed under low temperature conditions, which reduce degradation.

EXAMPLE 4

Dry Powder Inhalers

Metered dose and the dry powder formulations of the invention may be used directly in metered dose or dry powder inhalers.

A metered dose inhaler consists of three components: a canister containing the propellant drug suspension, a metering valve designed to deliver accurately metered volumes of the propellant suspension, and an oral adapter which contains a spray orifice from which the metered dose is delivered. In the rest position, the metering chamber of the valve is connected to the drug suspension reservoir via a filling groove or orifice. On depression of the valve this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber which is constituted by the internal volume of the valve stem and the oral adapter. The mixture undergoes further expansion before being expelled, under its own pressure, from the spray nozzle. On exit from the spray orifice, the liquid ligaments which are embedded in propellant vapor are torn apart by aerodynamic forces. Typically, at this stage, the droplets are 20 to 30µ in diameter and are moving at the velocity of sound of the two-phase vapor liquid mixture (approximately 30 meters per second). As the cloud of droplets moves away from the spray nozzle, it entrains air from its surroundings and decelerates, while the propellant evaporates through evaporation and the entrained droplets eventually reach their residual diameter.

At this point, the particles/droplets consist of a powdered drug core coated with surfactant. Depending on the concentration and the size of the suspended material the powdered drug core consists of either individual drug particles or aggregates. Currently, meter dose inhaler technology is optimized to deliver masses of 80 to 100 micrograms of drug, with an upper limitation of 1 mg of drug deliverable.

An alternated route of dry powder delivery is by dry powder inhalers. There are two major designs of dry powder inhalers, device-metering designs in which a reservoir of drug is stored within the device and the patient "loads" a dose of the device into the inhalation chamber, and factory-metered devices in which each individual dose has been manufactured in a separate container. Both systems depend upon the formulation of drug into small particles of mass median diameters from 1 to 5 microns, and usually involve co-formulation with large excipient particles (typically 100 micron diameter lactose particles). Drug powder is supplied into the inhalation chamber (either by device metering or by breakage of a factory-metering dosage) and the inspiratory flow of the patient accelerates the powder out of the device and into the oral cavity. Non-laminar flow characteristics of the powder path cause the excipient-drug aggregate to decompose, and the mass of the large excipient particles causes their impaction at the back of the throat, while the inhaler drug particles are deposited deep in the lungs. Current technology for dry powder inhalers is such that payload limits are around 50 mg of powder (of which drug is usually a partial component by mass). Excipients commonly used are lactose, however in the current case aztreonam is reacted with amino acid lysine and such reaction leads to a better powder formation and more stable powder formulation.

Effective dosage levels of aztreonam lysinate antibiotic for dry powder inhalation and metered dose inhalation result in the delivery of at least about 25 mg, and more preferable about 50 to about 100 mg of aztreonam lysinate to the lung of the patient receiving treatment. Depending on the efficiency of the dry powder delivery device, dry powder formulations suitable for use in the invention comprise from about 1.0 to about 250 mg, preferably from about 10 to about 100 mg of powder in an amorphous or crystalline state in particle sizes between 1 and 5 microns in mass median average diameter necessary for efficacious delivery of the antibiotic into the endobronchial space.

EXAMPLE 5

Preparation of Aztreonam Lysinate Salt

This example describes procedure used for preparation of aztreonam lysinate salt.

To a solution of 10 g (23 mmol) of aztreonam lysinate in 100 mL of MeOH cooled in an ice bath was added dropwise 23 mL (23 mmol, 1.0 eq) of 1N sodium hydroxide solution. The resulting solution was warmed to ambient temperature over a period of 30 min, and then the solvent was removed under reduced pressure. Diethylether (50 mL) was added and the slurry concentrated. This step was repeated four times to provide a yield of 10.1 g (96%) of aztreonam lysinate salt as a white powder.

EXAMPLE 6

Formulation and Spray Drying of Aztreonam (from Alpha Form) Lysinate

Aztreonam (alpha form, 29.4 g with 15% moisture, equivalent to 25.0 g anhydrous) was suspended and rapidly stirred in water (190 mL) and cooled with a crushed ice bath. L-Lysine (anhydrous, 17.7 g, dissolved in 40 mL of room temperature water) was titrated over 6 minutes to the milky white suspension to obtain a pH of 4.34. The total volume of the aztreonam lysinate solution was approximately 270 mL and had a yellow to light brown color. Approximately 1 g of charcoal was added to the stirring solution and was then filtered. The aztreonam lysinate solution was kept at 2 to 10° C. Spray drying was accomplished giving a yield of 22.2 g (56%) of aztreonam lysinate. Below illustrates an unoptimized method for spray drying:

Inlet Set 135° C.
Aspirator 90% (a value of 100%=35 cubic meters/hr).
Pump 34% (a value of 100%=1500 mL/hr).
Ar flow at nozzle 400 L/hr initial; at middle of run increased to 600 L/hr.
Receiver flask temp 35 to 40° C.

EXAMPLE 7

Testing Nebulizers

This example describes testing of nebulizers in clinical conditions to determine dose to be used in each.

A clinical study is conducted in order to determine the concentration of aztreonam lysinate in the aerosol formulation required to achieve a sputum concentration between 500 µg/gm and 2000 µg/gm sputum at 10 min post-completion of aerosol administration using an atomizing, ultrasonic or jet nebulizer.

In this study, cystic fibrosis patients receive serial escalating doses of multiple of 75 mg aztreonam lysinate (1 ml of a 75 mg/ml solution in ¼ NS) from each of the nebulizers. The doses are separated by at least 2 days and not more than 5 days. Peak serum and sputum concentrations are assessed.

EXAMPLE 8

Testing of Sputum Inhibitory Activity

This example describes conditions used for testing inhibitory activity of aztreonam lysinate and tobramycin on sputum or hog gastric mucin.

Reagents

Unless stated otherwise, all chemicals were purchased from Sigma Chemical Company (St. Louis, Mo.), and all solutions were prepared in sterile deionized water. Aztreonam (Azactam®) were obtained from Elan Biopharmaceuticals. Aztreonam lysinate was prepared at Corus Pharma, Seattle, Wash. Working stock solutions of aztreonam and aztreonam lysinate were prepared in sterile deionized water and used immediately.

Culture Medium

Divalent cation adjusted Mueller Hinton broth (CAMHB) was purchased from PML and used both as the, study growth medium for *P. aeruginosa* and as the assay growth medium.

Sputum

Sputum was obtained from children and adults with CF who were not receiving any other antimicrobial drug for at least 48 hours prior to the collection of the sample. Sputum was sterilized by stirring with a magnetic stirrer under UV light for 4 hours. Sterility was tested by inoculating 100 uL of sputum into 10 mLs of CAMHB a row medium and incubating overnight. Resulting culture was examined for turbidity and 100 muL were plated on Luria agar to ensure sterility. The sputum samples were kept frozen at −20° C. until used.

Organisms

Fresh subcultures of *P. aeruginosa* strain PA27853 were used for each experiment. Freezer stock was grown on Luria agar plates (Sigma L-3522) overnight at 37° C. A single colony was picked and inoculated into 5 mL of CAMHB and grown for 16 hours at 37° C. with shaking at 250 rpm. This overnight culture was diluted 1:10,000 in fresh CAMHB or in fresh CAMHB supplemented with 10% (w/v) porcine gastric mucin (Sigma M-1778), then autoclaved, or 1% sterilized CF sputum.

Killing Curves

P. aeruginosa (initial density ~$10^6$ CFU/mL) was grown in overnight culture and diluted 1:10,000 in broth. The dilutions were each divided into 4 tubes (10 mL per tube) and antibiotic was added to each tube to a final concentration of 0, 0.1, 1, and 10 times the MIC for strain PA27853 (4 μg/mL for aztreonam, 1.56 μg/mL for tobramycin, determined by standard methods). Each tube was incubated at 37° C. with 250 rpm shaking. Each hour, samples were removed from the tube, diluted, and plated on Luria agar for quantitation. Plates were incubated overnight at 37° C. and colonies were counted by hand.

EXAMPLE 9

Clinical Trial Protocol

This example describes a protocol used for clinical trial and to compare the pharmacokinetics of increasing dosage of an aztreonam lysinate formulation administered by the PARI electronic nebulizer to patients with cystic fibrosis.

The primary aim of this study was to determine which of the tested dose levels delivered by aerosol can deliver sufficient amount of aztreonam lysinate to achieve a mean peak sputum aztreonam lysinate concentration of 1000 μg/gm or greater measured 10 minutes after the completion of nebulization in patients with CF.

The secondary aim was to determine whether the aztreonam lysinate concentration required to achieve a mean peak sputum concentration of 1000 μg/gm or greater is safe and well tolerated by the patient.

Study Design

This was an open label, multicenter, randomized, dose escalation study.

Each arm contained different dose. Two arms delivered the same aztreonam lysinate formulation.
1. 1.0 ml of aztreonam lysinate solution of 75 mg/ml
2. 2.0 ml of aztreonam lysinate solution of 75 mg/ml
3. 3.0 ml of aztreonam lysinate solution of 75 mg/ml Efficacy and Safety Assessment In this study, the following efficacy and safety parameters that were assessed were:

The efficacy was determined for each nebulizer by measuring concentration of aztreonam lysinate in sputum 10 minutes after completion of nebulization. Mean concentration of 1000 μg/gm of sputum was considered adequate.

The safety parameters assessed:
1. Incidence of treatment related adverse reactions occurring during the administration of the aerosolized aztreonam lysinate at the different dose levels.
2. Acute bronchospasm at the time of drug administration.
3. Absorption of aztreonam lysinate into the systemic circulation.

Each patient received in random order at least one administration. Each aerosol administration was separated by a minimum of 48 hr. Sputum samples were collected at baseline, 1, 2, 4 and 6 hours post-completion of the aerosol drug administration to measure aztreonam lysinate concentration. Serum samples were collected at baseline, 1, 2, 4 and 6 hours post-completion of aerosol administration to measure aztreonam lysinate levels.

Airway irritation and acute bronchospasm were assessed by measuring spirometry immediately prior to and 30 min post-completion of aerosol administration. A decrease in forced expired volume in one second (FEV1) >15% in the 30 min spirometry test is considered evidence of bronchospasm.

Additional objectives of this study were to determine and at what dose the PARI electronic nebulizer tested can aerosolize sufficient aztreonam lysinate sulfate to achieve a mean peak sputum aztreonam lysinate concentration of 1000 μg/gm or greater in at least 85% of patients with CF measured 10 minutes after the completion of nebulization to determine whether the aztreonam lysinate concentration required to achieve a mean peak sputum concentration of 1000 μg/gm or greater is safe and well tolerated by the patient. Safety is defined as a lack of acute bronchospasm and minimal systemic absorption.

Patient Treatment

All patients with underlying disease of cystic fibrosis (CF), confirmed at entry by the inclusion/exclusion criteria specified in this protocol, were eligible for enrollment into the study. Investigators at the participating CF centers selected patients that meet all of the inclusion criteria and one of the exclusion criteria.

Eligible patients were admitted to the study center on the day of the study and receive aerosol therapy if they fulfilled entrance criteria.

Physical exam is administered by a physician or RC nurse prior to initial aerosol treatment only.

Vital signs, height, weight, oximetry, assessment of current respiratory status and brief medical history were used. Sputum and serum samples were collected to measure baseline aztreonam lysinate concentrations.

Patients were sitting upright and use nose clips during the aerosol administration.

The total duration of time and the number of inhalations required to complete the aerosol treatment were recorded.

Any evidence of wheezing or respiratory distress are recorded as well as number of rest periods required by the subject because of dyspnea or excessive coughing during the administration period.

Immediately after completing the aerosol therapy, the subject rinsed with 30 ml of normal saline through the mount, gargled for 5–10 seconds and expectorated the rinse. This was repeated for a total of three rinses.

Sputum specimens were collected at 10 minutes after rinsing oral cavity and 2 hours after completion of the aerosol drug administration.

Serum was collected at 1 and 2 hours after completion of the aerosol drug administration for determination of the aztreonam lysinate levels.

Spirometry was obtained 30 minutes following completion of the aerosol drug administration.

Following the last aerosol treatment of the study, patients received a brief physical exam after post-spirometry has been measured.

EXAMPLE 10

Safety Clinical Trials

This example describes clinical protocol used for safety clinical trial with aztreonam lysinate.

Name of Finished Product: Aztreonam for Inhalation

Name of Active Ingredient: Aztreonam lysinate.

This was a randomized, double-blind, placebo controlled trial to assess the safety and tolerability of inhaled aztreonam lysinate in healthy male and female volunteers.

The primary objective was to determine the safety and tolerability of 3 escalating doses of aztreonam for inhalation in male and female volunteers.

Methodology

Subjects were screened for inclusion in the trial up to 21 days before dosing and their eligibility was confirmed at the day 1 visit. Subjects were admitted to the clinic in the morning on the day before dosing (Day −1). Within each of the 3 treatments groups receiving 95 mg, 190 mg and 285 mg inhaled aztreonam, subjects were allocated randomly to either active treatment (6 subjects) or to placebo (2 subjects). Progression to the 190 mg and 285 mg doses occurred only when blinded safety data from the 95 mg and 190 mg groups, respectively, had been assessed. On the morning of day 1, subjects self-administered their allocated trial medication by inhalation using an eFlow™IMP nebulizer (PARI). Subjects remained in the clinic for 24 h after dosing and returned 3 days after dosing for a follow-up visit. Safety was monitored throughout the trial.

Number of Subjects 24 subjects (3 groups of 8 subjects) were recruited and 24 were included in the safety analysis.

Diagnosis and Main Criteria for Inclusion

Subjects were male or female non-smokers, aged 18 to 55, weighing between 50 and 100 kg with a body mass index of 18 to 28 kg.m$^{-2}$, with a negative Coombs' test result and a forced expiratory volume in one second (FEV$_1$) of at least 80% of the predicted normal.

Test Product, Dose and Mode of Administration

Placebo (1, 2 or 3 ml sterile 0.9% saline; manufactured by Phoenix Pharma, was self-administered by the subject into the airways using an eFlow™IMP nebulizer (PARI).

Safety

Adverse events, laboratory data (hematology, clinical chemistry, Coombs' test, coagulation and pregnancy test for women of childbearing potential), urinalysis, vital signs, ECG, physical examination (including chest auscultation) and pulmonary function tests.

Safety Results

No serious adverse events were recorded during the trial and no subject was withdrawn from the trial because of an adverse event.

EXAMPLE 11

Beagle Dog Safety Study

This example describes conditions used for Beagle dog safety studies.

Sixteen male and female Beagle dogs were allocated to 4 dose groups and treated as follows:

| Dose Group/ Treatment | Target Dose Levels (mg . kg$^{-1}$ . day$^{-1}$) Total | Pulmonary | Animal Numbers/Allocation | Males | Females |
|---|---|---|---|---|---|
| 1-Vehicle Control | 0 | 0 | Main Study | 1–3 | 17–19 |
|  |  |  | Recovery | 4–5 | 20–21 |
| 2-Low Dose | 40 | 8 | Main Study | 6–8 | 22–24 |
| 3-Intermediate Dose | 80 | 16 | Main Study | 9–11 | 25–27 |
| 4-High Dose | 200 | 40 | Main Study | 12–14 | 28–30 |
|  |  |  | Study Recovery | 15–16 | 31–32 |

During the pretrial and recovery phases of the study animals were monitored at least once daily for any adverse clinical signs. During the treatment period, all animals were examined for any adverse clinical signs before exposure, continuously during exposure and at cca 1–2 h after exposure. Body weights were recorded weekly whilst food consumption was monitored daily up until the end of the study period.

Ophthalmoscopic examinations were undertaken once pretrial, during Week 4 of treatment and towards the end of the 14 day recovery period for designated animals. Electrocardiograms were recorded once pretrial, on Days 2 and 28 of treatment and from designated recovery animals towards the end of the 14 day recovery period.

Blood and urine samples for routine hematology, clinical chemistry and urinalysis investigations were obtained from all animals once pretrial, during Week 4 of treatment, and from designated recovery animals towards the end of the 14 day recovery period. Blood samples for toxicokinetic analysis were collected from all animals from Groups 2, 3 and 4 on Days 1 and 27 of exposure at the following target timepoints: predose, immediately post dose (IPD) and at 0.25, 0.5, 1, 2, 4, 6, 8 and 24 h post dose. Samples were collected from Group 1 animals predose and immediately post dose. Urine samples for toxicokinetic analysis were collected from all animals on Days 1 and 27 of exposure over a 24 h period.

On completion of the 28/29 day treatment period or 14 day recovery period, all animals were subjected to a detailed necropsy with recording of organ weights. Microscopic evaluation was undertaken on a comprehensive list of tissues.

Overall estimated mean achieved doses of 0, 53.0, 94.3 and 194.7 mg.kg$^{-1}$.day$^{-1}$ (estimated mean pulmonary doses of 0, 10.6, 18.9 and 38.9 mg.kg$^{-1}$.day$^{-1}$) were achieved for Groups 1, 2, 3 and 4, respectively. Particle size distribution measurements indicated the Aztreonam aerosol was respirable for dogs.

Treatment described herein was safe method for any sign of adverse reaction.

What is claimed is:

1. An inhalable composition comprising aztreonam lysinate, said composition suitable for the treatment of pulmonary bacterial infections caused by gram-negative bacteria, wherein said aztreonam lysinate is prepared as an inhalable dry powder having a particle size with a mass medium average diameter from about 1 to about 5μ.

2. The composition of claim 1 wherein the aztreonam lysinate is alpha aztreonam lysinate.

3. The composition of claim 1 wherein the gram-negative bacteria is *Burkholderia cepacia*.

4. The composition of claim 1 wherein the gram-negative bacteria is *Stenotrophomonas maltophilia*.

5. The composition of claim 1 wherein the gram-negative bacteria is *Alcaligenes xylosoxidans*.

6. The composition of claim 1 wherein the gram-negative bacteria is a multidrug resistant *Pseudomonas aeruginosa*.

7. The composition of claim 1 comprising from about 1 to 250 mg of the aztreonam lysinate, wherein the composition may be administered as the inhalable dry powder by a dry powder inhaler or as a diluted saline solution by a metered dose inhaler the aerosolable solution.

8. The composition of claim 7, comprising 10 to 100 of aztreonam lysinate.

9. The composition of claim 8 comprising 75 mg of aztreonam lysinate, wherein said composition may be administered twice or three times a day.

10. The composition of claim 7 wherein the aztreonam lysinate is alpha aztreonam lysinate prepared from an alpha aztreonam form.

11. The composition of claim 10 wherein said alpha aztreonam lysinate has impurity lower than 1% and stability for at least two years.

12. The composition of claim 11 wherein said alpha aztreonam lysinate contains less than 100 ppm of residual alcohol and initial levels of contaminants generated from the alpha aztreonam lysinate are less than 1%.

13. The composition of claim 10 wherein said aztreonam lysinate is in a solution comprising a volume of saline from about 1 to about 5 ml, said saline comprising between about 0.09% and about 0.9% of chloride, w/v, or an equivalent amount of bromine or iodine, wherein said solution is aerosolable and wherein said aerosolable solution has a pH from about 4.2 to about 7.5.

14. The composition of claim 13 wherein said saline comprises from about 0.1 to about 0.45% of sodium chloride, w/v, and wherein said pH is from about 5.5 to about 7.

15. The composition of claim 14 wherein the aztreonam lysinate is present in a concentration of about 75 mg/ml in said saline.

16. A method for administering aztreonam lysinate comprising administration of the composition of claim 7 by a dry powder inhaler or by a metered dose inhaler, wherein said composition may be administered one to twelve times a day, provided that if the composition is delivered more than twice a day, a total dose of aztreonam lysinate is not higher than 750 mg a day.

* * * * *

UNITED STATES PATENT AND TRADEMARK OFFICE
CERTIFICATE OF CORRECTION

| | |
|---|---|
| PATENT NO. | : 7,214,364 B2 |
| APPLICATION NO. | : 10/613639 |
| DATED | : May 8, 2007 |
| INVENTOR(S) | : Alan Bruce Montgomery |

It is certified that error appears in the above-identified patent and that said Letters Patent is hereby corrected as shown below:

At column 5, line 26, delete "lysinate".

At column 6, line 54, delete "lysinate".

At column 13, line 55, insert -- of aztreonam -- between "mg/mL" and ",".

At column 13, line 56, insert -- of aztreonam -- between "mg/mL" and ",".

At column 16, line 42, delete "lysinate".

At column 16, line 49, delete "lysinate".

At column 16, line 60, delete "lysinate".

At column 16, line 61, delete "lysinate".

At column 17, line 2, delete "lysinate".

At column 36, line 24, delete "lysinate".

At column 37, line 40, after the word "solution", delete "of" and insert therefor -- containing --.

At column 37, line 40, insert -- of aztreonam -- after "mg/ml".

At column 37, line 41, after the word "solution", delete "of" and insert therefor -- containing --.

At column 37, line 41, insert -- of aztreonam -- after "mg/ml".

At column 37, line 42, after the word "solution", delete "of" and insert therefor -- containing --.

At column 37, line 42, insert -- of aztreonam -- after "mg/ml".

At column 40, line 47, i.e., the 6th line of Claim 1, "5μ" should read -- 5μm --.

At column 40, line 60, i.e., the third line of Claim 7, "may be" should read -- is --.

At column 40, line 60, i.e., the third line of Claim 7, "the" should read -- an --.

UNITED STATES PATENT AND TRADEMARK OFFICE
CERTIFICATE OF CORRECTION

PATENT NO. : 7,214,364 B2
APPLICATION NO. : 10/613639
DATED : May 8, 2007
INVENTOR(S) : Alan Bruce Montgomery It is certified that error appears in the above-identified patent and that said Letters Patent is hereby corrected as shown below:

At column 40, line 61, i.e., the 4th line of Claim 7, after the word "as", "a" should read -- an aerosolable --.

At column 40, line 62, i.e., the 5th line of Claim 7, delete "the aerosolable solution".

At column 40, line 63, i.e., the first line of Claim 8, insert -- mg -- between "10 to 100" and "of".

At column 40, line 65, i.e., the first line of Claim 9, after the word "claim", delete "7" and insert therefor -- 8 --.

At column 40, line 66, i.e., the second line of Claim 9, delete "lysinate".

At column 41, line 14, i.e., the 4th line of Claim 13, insert -- sodium -- between "of" and "chloride".

At column 42, line 6, i.e., the second line of Claim 15, delete "lysinate".

Signed and Sealed this

Third Day of June, 2008

JON W. DUDAS
*Director of the United States Patent and Trademark Office*

UNITED STATES PATENT AND TRADEMARK OFFICE
Certificate

Patent No. 7,214,364 B2 — Patented: May 8, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Alan Bruce Montgomery, Medina, WA (US); Manfred Keller, Munchen (DE); and Frank-Christophe Lintz, Starnberg (DE).

Signed and Sealed this Twenty-seventh day of April 2010.

JOHANN R. RICHTER
*Supervisory Patent Examiner*
Art Unit 1616